(12) United States Patent
Macintyre et al.

(10) Patent No.: US 12,367,980 B2
(45) Date of Patent: Jul. 22, 2025

(54) METHODS FOR PREDICTING TREATMENT RESPONSE IN CANCERS

(71) Applicant: Cancer Research Technology Limited, London (GB)

(72) Inventors: Geoff Macintyre, London (GB); James Brenton, London (GB); Anna Piskorz, London (GB); Florian Markowetz, London (GB)

(73) Assignee: Cancer Research Technology Limited, London (GB)

( * ) Notice: Subject to any disclaimer, the term of this patent is extended or adjusted under 35 U.S.C. 154(b) by 159 days.

(21) Appl. No.: 18/007,670

(22) PCT Filed: Jun. 4, 2021

(86) PCT No.: PCT/EP2021/065058
§ 371 (c)(1),
(2) Date: Dec. 1, 2022

(87) PCT Pub. No.: WO2021/245265
PCT Pub. Date: Dec. 9, 2021

(65) Prior Publication Data
US 2024/0062898 A1    Feb. 22, 2024

(30) Foreign Application Priority Data
Jun. 4, 2020    (GB) .................................... 2008450

(51) Int. Cl.
*G16H 50/20*    (2018.01)
*G16B 20/10*    (2019.01)
(Continued)

(52) U.S. Cl.
CPC ............ *G16H 50/20* (2018.01); *G16B 20/10* (2019.02); *G16H 10/40* (2018.01); *G16H 20/10* (2018.01)

(58) Field of Classification Search
None
See application file for complete search history.

(56) References Cited

U.S. PATENT DOCUMENTS 5,804,414 A * 9/1998 Moriya .................. C12P 13/08
435/106
2011/0105341 A1    5/2011    Semizarov et al.

FOREIGN PATENT DOCUMENTS

| WO | WO-2014055543 A2 * | 4/2014 | .......... A61K 31/519 |
| WO | WO 2017/191074 A1 | 11/2017 | |
| WO | WO 2017/211947 A1 | 12/2017 | |

OTHER PUBLICATIONS

"Copy Number Alterations in Tumor Genomes Deleting Antineoplastic Drug Targets Partially Compensated by Complementary Amplifications"; Tran et al. Cancer Genomics & Proteomics; Jul. 2018. (Year: 2018).*

(Continued)

*Primary Examiner* — John A Pauls
(74) *Attorney, Agent, or Firm* — Klarquist Sparkman, LLP

(57) ABSTRACT

The present invention provides methods for predicting the treatment response of a cancer patient, using a tumour copy number profile for the patient. The method comprise analysing the copy number profile to assess whether the characteristics of at least one copy number feature are indicative of the presence of focal amplifications in the tumour genome, wherein the at least one copy number feature is selected from: copy number change-point, segment size and segment copy number. The patient is predicted as being likely to be resistant to treatment with an agent that induces the formation of micronuclei (e.g. doxorubicin) if the characteristics of the at least one copy number features are indicative of the presence of focal amplifications in the tumour genome. Also provided a related methods and systems.

20 Claims, 6 Drawing Sheets

(51) Int. Cl.
  *G16H 10/40* (2018.01)
  *G16H 20/10* (2018.01)

(56) References Cited

OTHER PUBLICATIONS

Davoli et al., "Tumor aneuploidy correlates with markers of immune evasion and with reduced response to immunotherapy," *Science*, vol. 355, No. 6322, pp. 1-33, 2017 (Author manuscript version).
Dugo et al., "Focal Recurrent Copy Number Alterations Characterize Disease Relapse in High Grade Serous Ovarian Cancer Patients with Good Clinical Prognosis: A Pilot Study," *Genes*, 10:678, 2019 (16 pages).
MacIntyre et al., "Copy number signatures and mutational processes in ovarian carcinoma," *Nature Genetics*, vol. 50, pp. 1262-1270, 2018.
Alberts et al., "Randomized Trial of Pegylated Liposomal Doxorubicin (PLD) Plus Carboplatin Versus Carboplatin in Platinum-Sensitive (PS) Patients With Recurrent Epithelial Ovarian or Peritoneal Carcinoma After Failure of Initial Platinum-Based Chemotherapy (South West Oncology Group Protocol S0200)," *Gynecol Oncol.*, vol. 108, No. 1, pp. 90-94, 2008 (Author manuscript version, 11 pages).
Alexandrov et al., "Signatures of mutational processes in human cancer," *Nature*, vol. 500, pp. 415-421, 2013.
Alexandrov et al., "The repertoire of mutational signatures in human cancer," *Nature*, vol. 578, pp. 94-101, 2020.
Bafaloukos et al., "A randomized phase II study of carboplatin plus pegylated liposomal doxorubicin versus carboplatin plus paclitaxel in platinum sensitive ovarian cancer patients: a Hellenic Cooperative Oncology Group study," *BMC Medicine*, 8:3, 2010 (12 pages).
Broad Institute, "Picard toolkit," http://broadinstitute.giyhub.io/picard/, 2018 (7 pages).
Ferrandina et al., "Phase III Trial of Gemcitabine Compared With Pegylated Liposomal Doxorubicin in Progressive or Recurrent Ovarian Cancer," *Journal of Clinical Oncology*, vol. 26, No. 6, pp. 890-896, 2008.
Gordon et al., "Long-term survival advantage for women treated with pegylated liposomal doxorubicin compared with topotecan in a phase 3 randomized study of recurrent and refractory epithelial ovarian cancer," *Gynecologic Oncology*, vol. 95, pp. 1-8, 2004.
Gordon et al., "Recurrent Epithelial Ovarian Carcinoma: A Randomized Phase III Study of Pegylated Liposomal Doxorubicin Versus Topotecan," *Journal of Clinical Oncology*, vol. 19, No. 14, pp. 3312-3322, 2001.
Grun et al., "FlexMix Version 2: Finite Mixtures with Concomitant Variables and Varying and Constant Parameters," *Journal of Statistical Software*, vol. 28, No. 4, pp. 1-35, 2008.
Kassambara et al., survminer: Drawing Survival Curves using 'ggplot2,' https://CRAN.Rproject.org/pack age=survminer, 2019 (2 pages).
Kaye et al., "Phase II, Open-Label, Randomized, Multicenter Study Comparing the Efficacy and Safety of Olaparib, a Poly (ADP-Ribose) Polymerase Inhibitor, and Pegylated Liposomal Doxorubicin in Patients With BRCA1 or BRCA2 Mutations and Recurrent Ovarian Cancer," *Journal of Clinical Oncology*, vol. 30, pp. 372-379, 2011.
Li et al., "Fast and accurate short read alignment with Burrows-Wheeler transform," *Bioinformatics*, vol. 25, pp. 1754-1760, 2009.
Mutch et al., "Randomized Phase III Trial of Gemcitabine Compared With Pegylated Liposomal Doxorubicin in Patients With Platinum-Resistant Ovarian Cancer," *Journal of Clinical Oncology*, vol. 25, pp. 2811-2818, 2007.
Pujade-Lauraine et al., "Bevacizumab Combined With Chemotherapy for Platinum-Resistant Recurrent Ovarian Cancer: The AURELIA Open-Label Randomized Phase III Trial," *Journal of Clinical Oncology*, vol. 32, No. 13, pp. 1302-1308, 2014.
Ritz et al., "Dose-Response Analysis Using R," *PloS One*, 10:e0146021, 1-13, 2015.
Rose et al., "Phase 3 Study: Canfosfamide (C, TLK286) plus carboplatin (P) vs liposomal doxorubicin (D) as 2nd line therapy of platinum (P) resistant ovarian cancer (OC)," *Journal of Clinical Oncology*, vol. 25, No. 18 Suppl., LBA5529, 2007 (Abstract).
Rustin et al., "Definitions for Response and Progression in Ovarian Cancer Clinical Trials Incorporating RECIST 1.1 and CA 125 Agreed by the Gynecological Cancer Intergroup (GCIG)," *Int J Gynecol Cancer*, vol. 21, pp. 419-423, 2011.
Scheinin et al., "DNA copy number analysis of fresh and formalin-fixed specimens by shallow whole-genome sequencing with identification and exclusion of problematic regions in the genome assembly," *Genome Research*, vol. 24, pp. 2022-2032, 2014.
Schulze et al., "Exome sequencing of hepatocellular carcinomas identifies new mutational signatures and potential therapeutic targets," *Nature Genetics*, vol. 47, No. 5, pp. 505-511, 2015.
Therneau TM., "A Package for Survival Analysis in R,". https://CRAN.R-project.org/package=survival, 2020 (4 pages).

\* cited by examiner

METHODS FOR PREDICTING TREATMENT RESPONSE IN CANCERS

CROSS REFERENCE TO RELATED APPLICATIONS

This is the § 371 U.S. National Stage of International Application No. PCT/EP2021/065058, filed Jun. 4, 2021, which was published in English under PCT Article 21(2), which in turn claims the benefit of Great Britain Application No. 2008450.5, filed Jun. 4, 2020, which is incorporated herein by reference in its entirety.

FIELD OF THE INVENTION

The present invention relates in part to methods for predicting cancer response to chemotherapies based on features of copy number variation, particularly in cancers with high chromosomal instability such as ovarian cancer, and in relation to chemotherapies that induce the formation of micronuclei, such as e.g. doxorubicin.

BACKGROUND TO THE INVENTION

Lung, ovarian, oesophageal, sarcoma, glioblastoma and pancreatic cancers are deadly types of cancers, for which minimal improvements in survival have been seen for the last 40 years. These cancers are characterised by extreme chromosomal instability which results in several 'actionable' hits from gene panel-based tests. However, due to their unstable genomes, these cancers often have low frequency of recurrent oncogenic mutations, few recurrent copy number alterations, and highly complex genomic profiles. As a result, hits from gene panel-based tests are frequently false positives and targeted agents often fail to prove effective.

For ovarian cancers, current genomic stratification is limited to defining homologous recombination-deficient (HRD) tumours, with approximately 20% of high-grade serous ovarian cancer (HGSOC) having a BRCA1/2 mutation. Standard of care for ovarian cancer is typically a combination of chemotherapy (with carboplatin and paclitaxel) and debulking surgery. Patients which relapse within 6 months are considered platinum resistant while those who do not are considered platinum sensitive. However, 80% of all patients will eventually see their disease return. Platinum resistant patients will then receive paclitaxel as a monotherapy, followed by doxorubicin if they fail to respond to paclitaxel. Platinum sensitive patients will undergo another around of carboplatin but this time in combination with doxorubicin. This means that nearly all patients will receive doxorubicin at some stage. However the response rate to doxorubicin is low (18% in platinum resistant and 52% in platinum sensitive; Mutch et al., 2012; Kaye et al., 2012; Ferrandina et al., 2008; Gordon et al., Puiade-Lauraine et al., 2012; Rose et al., 2007; Bafaloukos et al., 2010; Alberts et al., 2008; O'Byrne et al., 2002). Evidence has suggested that patients with BRCA1/2 mutations are likely to respond slightly better, but the effect is small (Kaye et al., 2012).

While analysis of cancer genomes shows promise in the field of cancer care, there remains an unmet need for methods to predict treatment response of patients with cancers showing high chromosomal instability. The present invention seeks to provide solutions to these needs and provides further related advantages.

BRIEF DESCRIPTION OF THE INVENTION

The present inventors have previously demonstrated that copy-number signatures representing the genome-wide imprint of distinct mutational processes could be identified in cancers that have high chromosomal instability, such as HGSOC. They further found that copy-number signature exposures at diagnosis were predictive of overall survival and that signature 1 exposure was predictive of platinum-resistant relapse in HGSOC. Here, the inventors hypothesised that one of these signatures, characterised by copy-number features thought to be indicative of focal amplification, may be associated with the presence of micronuclei during the evolution of a tumour. They further hypothesised that the presence of this signature in a tumour may indicate that the tumour can tolerate micronuclei formation, and as such may be resistant to genotoxic chemotherapies that induce the formation of micronuclei, such as DNA intercalating agents and in particular DNA intercalating agents that act as topoisomerase II-poison. They found that presence of genome-wide copy-number features indicative of focal amplifications was associated with resistance to doxorubicin, a DNA intercalating agent that acts as a topoisomerase II-poison and induces the formation of micronuclei, in ovarian cancer. This supports the likely association between the signature and the presence of, and tolerance to, micronuclei, and hence indicates that the presence of this signature can be used to predict resistance to drugs that induce micronuclei.

Accordingly, in a first aspect the present invention provides a method for predicting the treatment response of a cancer patient, the method comprising:
(a) obtaining a tumour copy number profile for the patient; and
(b) analysing the copy number profile to assess whether the characteristics of at least one copy number feature are indicative of the presence of focal amplifications in the tumour genome;
wherein the at least one copy number feature is selected from: copy number change-point, segment size and copy number; and wherein the patient is predicted as being likely to be resistant to treatment with an agent that induces the formation of micronuclei if the characteristics of the at least one copy number features are indicative of the presence of focal amplifications in the tumour genome.

The patient is preferably a patient diagnosed as having or being likely to have a cancer with high chromosomal instability. The patient may be a patient diagnosed as having a carcinoma or a sarcoma. The patient may be a patient diagnosed as having glioblastoma, lung cancer, oesophageal cancer, pancreatic cancer, breast cancer or ovarian cancer. The patient preferably has high grade serous ovarian cancer (HGSOC) or triple negative breast cancer. The tumour copy number profile for the patient may have been obtained from a tumour sample from the patient or from a liquid biopsy sample from the patient, such as e.g. a blood or plasma sample.

The agent that induces the formation of micronuclei may be a genotoxic chemotherapeutic agent. The agent that induces the formation of micronuclei may be a genotoxic chemotherapeutic agent that acts as a DNA intercalating agent and/or a topoisomerase-II poison. The agent is preferably an anthracycline. The agent may be doxorubicin. The agent may be liposomal doxorubicin. The doxorubicin may be pegylated doxorubicin or non-pegylated doxorubicin.

Analysing the copy number profile to assess whether the characteristics at least one copy number feature are indicative of the presence of focal amplifications in the tumour genome may comprise:

i. quantifying, for each copy number event in the copy number profile, one or more copy number features selected from: the segment copy number, the copy number change-point, and the segment size; and ii. obtaining one or more summarised measures for each quantified copy number feature.

Analysing the copy number profile to assess whether the characteristics of at least one copy number feature are indicative of the presence of focal amplifications in the tumour genome may further comprise:

iii. quantifying, for each copy number event in the copy number profile the copy number change-point; and iv. obtaining one or more summarised measures for the copy number-change-point.

Analysing the copy number profile to assess whether the characteristics at least one copy number feature are indicative of the presence of focal amplifications in the tumour genome may comprise:

i. quantifying, for each copy number event in the copy number profile one or more further copy number features selected from: breakpoint count per x MB, where x is preferably 10, breakpoint count per chromosome arm, and length of segments with oscillating copy-number; and ii. obtaining one or more summarised measures for each further quantified copy number feature.

In embodiments, the one or more summarised measures comprise(s): for the copy number features selected from the segment copy number and the copy number change-point: a statistical measure of centrality of the distribution of values across copy number events, preferably the average or the median. In embodiments, the one or more summarised measures comprise(s): the number or proportion of values across copy number events that are above and/or below a predetermined threshold. In embodiments, the one or more summarised measures comprise(s): the maximum value across copy number events or the maximum value that is such that the proportion of copy number events that are at or above the value is above a predetermined threshold. In embodiments, the one or more summarised measures comprise(s): for the segment size copy number feature: the minimum value across copy number events or the minimum value that is such that the proportion of copy number events that are at or below the value is above a predetermined threshold. In embodiments, the one or more summarised measures comprise(s): the sum-of-posterior probabilities of the copy number feature value for each copy number event belonging to one or more predetermined distributions.

In embodiments, analysing the copy number profile to assess whether the characteristics of at least one copy number feature are indicative of the presence of focal amplifications in the tumour genome comprises: comparing the average, median or maximum segment copy number to a predetermined threshold, wherein the average, median or maximum segment copy number being above the predetermined threshold is indicative of the presence of focal amplifications in the tumour genome, preferably wherein the predetermined threshold is determined by comparing the average, median or maximum segment copy number between resistant and sensitive samples in a training cohort. In embodiments, analysing the copy number profile to assess whether the characteristics of at least one copy number feature are indicative of the presence of focal amplifications in the tumour genome comprises: comparing the average, median or maximum copy number change-point to a predetermined threshold, wherein the average, median or maximum copy number change-point being above the predetermined threshold is indicative of the presence of focal amplifications in the tumour genome, preferably wherein the predetermined threshold is determined by comparing the average or median copy number change-point between resistant and sensitive samples in a training cohort.

In embodiments, the predetermined threshold is determined by comparing the average, median or maximum copy number change-point (or segment copy number) between resistant and sensitive samples in a training cohort and identifying the threshold that results in the highest proportion of samples being correctly identified as resistant and sensitive (i.e. the threshold that maximises the accuracy of a classification using said threshold).

In embodiments, the predetermined threshold is determined by comparing the average, median or maximum copy number change-point (or segment copy number) between resistant and sensitive samples in a training cohort and identifying the threshold that results in the highest proportion of resistant samples being correctly identified as resistant while not wrongly identifying any sensitive sample as resistant (i.e. the threshold that maximises the specificity— true negative rate—of a classification using said threshold while having 100% sensitivity—true positive rate).

In embodiments, the predetermined threshold for the average segment copy number is between 2.65 and 3.60 (or between 2.8 and 3.4, between 3 and 3.2, or about 3.15, such as e.g. 3.146530). In embodiments, the predetermined threshold for the median segment copy number is 2.85 and 3.1 (or between 2.9 and 3.05, between 2.95 and 3.05, or about 3, such as e.g. 3.000824). In embodiments, the predetermined threshold for the maximum segment copy number is between 7 and 9 (or between 7.5 and 8.5, between 8 and 9, or about 8.5). In embodiments, the predetermined threshold for the average copy number change-point is between 1.2 and 1.328 (or between 1.2 and 1.328, between 1.3 and 1.328, or about 1.328, such as e.g. 1.323483). In embodiments, the predetermined threshold for the median copy number change-point is between 1.04 and 2.1, between 1.2 and 2.1, or between 1.04 and 1.06 (such as e.g. 1.051904). In embodiments, the predetermined threshold for the maximum copy number change-point is between 4.01 and 30, between 4.01 and 5 (or between 4.01 and 4.025), or between 17.6 and 18 (such as e.g. about 18), or between 18 and 30.

In embodiments, analysing the copy number profile to assess whether the characteristics at least one copy number feature are indicative of the presence of focal amplifications in the tumour genome comprises: comparing the number or proportion of events with a segment copy number above a first predetermined threshold to a second predetermined threshold, wherein the number or proportion of events being above the second predetermined threshold is indicative of the presence of focal amplifications in the tumour genome, preferably wherein the first and/or second predetermined thresholds are obtained by comparing the distribution of segment copy number for resistant and sensitive samples in a training cohort. In embodiments, analysing the copy number profile to assess whether the characteristics at least one copy number feature are indicative of the presence of focal amplifications in the tumour genome comprises: comparing the number or proportion of events with a copy number change-point above a first predetermined threshold to a second predetermined threshold, wherein the number or proportion of events being above the second predetermined threshold is indicative of the presence of focal amplifications in the tumour genome, preferably wherein the first and/or second predetermined thresholds are obtained by comparing the distribution of copy number change-point for resistant and sensitive samples in a training cohort.

In embodiments, analysing the copy number profile to assess whether the characteristics at least one copy number feature are indicative of the presence of focal amplifications in the tumour genome comprises: comparing (a) the proportion or number of events with a segment size above a first predetermined threshold to a second predetermined threshold, and (b) the proportion or number of events with a segment size below a third predetermined threshold to a fourth predetermined threshold, wherein the proportions in (a) and (b) being above their respective predetermined thresholds is indicative of the presence of focal amplifications in the tumour genome, or comparing the sum of the proportion or number of events with a segment size above a first predetermined threshold and the proportion or number of events with a segment size below a third predetermined threshold to a fifth predetermined threshold, preferably wherein the first, second, third, fourth and/or fifth predetermined thresholds are obtained by comparing the distribution of segment size for resistant and sensitive samples in a training cohort.

In embodiments, the predetermined threshold(s) is/are determined by comparing the distribution of segment size, copy number change-point and/or segment copy number between resistant and sensitive samples in a training cohort and identifying the threshold(s) that result(s) in the highest proportion of samples being correctly identified as resistant and sensitive (i.e. the threshold(s) that maximise(s) the accuracy of a classification using said threshold(s)).

In embodiments, the predetermined threshold(s) is/are determined by comparing the distribution of segment size, copy number change-point and/or segment copy number between resistant and sensitive samples in a training cohort and identifying the threshold(s) that result(s) in the highest proportion of resistant samples being correctly identified as resistant while not wrongly identifying any sensitive sample as resistant (i.e. the threshold(s) that maximises the specificity—true negative rate—of a classification using said threshold(s) while having 100% sensitivity—true positive rate).

In embodiments, the first predetermined threshold for segment copy number is 5 and the second predetermined threshold is between 36 and 60 (or between 36 and 50, between 38 and 48, between 40 and 45, such as e.g. 42) (for a number of events) and about 5% (or between 25 and 28%) (for a % of events). In embodiments, the first predetermined threshold for copy number change-point is 4 and the second predetermined threshold is between 2 and 18 (or between 2 and 8, between 2 and 6, such as e.g. 3) (for a number of events) and between 2% and 10% (or between 2 and 8%, such as e.g. 5% or between 8.6 and 10%, such as e.g. 8.6%) (for a % of events). In embodiments, the first predetermined threshold for segment size is 12,000,000 bp, and the third predetermined threshold for segment size is 4,000,000 bp. In some such embodiments, the second predetermined threshold for segment size is between 52 and 68, such as e.g. 52 or 68 (for a number of events). In some embodiments, the fourth predetermined threshold is between 55 and 214, such as e.g. 55 or 214 (for a number of events). In embodiments, the fifth predetermined threshold is 130 (for the sum of number of events).

Advantageously, the copy number features are characterised on a genome-wide basis.

In embodiments, analysing the copy number profile to assess whether the characteristics at least one copy number feature are indicative of the presence of focal amplifications in the tumour genome comprises: for each copy number feature quantified, comparing the sum-of-posterior probabilities of the copy number feature value for each copy number event belonging to one or more predetermined distributions to a respective predetermined threshold;
  wherein the one or more predetermined distributions comprise:
    a distribution (C1) of copy number change-point values centred around a value between 2 and 32, preferably between 4 and 30, between 5 and 30, or between 6 and 30;
    a distribution (C2) of copy number values centred around a value between 5 and 34, preferably between 6 and 34, between 7 and 34, between 6 and 32, between 7 and 32, or between 8 and 32; and/or
    a distribution (C3) of segment sizes centred around a value between 100,000 and 4,000,000 base pairs, preferably between 200,000 and 4,000,000 bp, between 300,000 and 4,000,000 bp, between 400,000 and 4,000,000 bp, between 100,000 and 3,000,000 bp, between 200,000 and 3,000,000 bp, between 300,000 and 3,000,000 bp, between 400,000 and 3,000,000 bp, between 100,000 and 2,500,000 bp, between 200,000 and 2,500,000 bp, between 300,000 and 2,500,000 bp or between 400,000 and 2,500,000 bp, and a distribution (C4) of segment sizes centred around a value between 12,000,000 and 80,000,000 bp, preferably between 15,000,000 and 60,000,000
  wherein the respective predetermined thresholds are quantified by comparing the sum-of-posterior probabilities for resistant and sensitive samples in a training cohort.

The distribution C1 is preferably a Gaussian distribution, such as a Gaussian distribution with a mean of about 28.7 (e.g. 28.7±10%) and a standard deviation of about 22.1 (e.g. 22.1±10%) (such as e.g. copy number change-point component 7, cp7, in Table 1), a Gaussian distribution with a mean of about 7.3 (e.g. 7.3±10%) and a standard deviation of about 3.4 (e.g. 3.4±10%) (such as e.g. copy number change-point component 6, cp6, in Table 1), or a Gaussian distribution with a mean of about 3.0 (e.g. 3.0±10%) and a standard deviation of about 1.0 (e.g. 1.0±10%) (such as e.g. copy number change-point component 5, cp5, in Table 1).

In embodiments, the predetermined threshold for the copy number change-point sum-of-posterior probabilities is 0.02041483.

In embodiments, the distribution C1 is a Gaussian distribution, such as a Gaussian distribution with a mean of about 28.7 (e.g. 28.7±10%) and a standard deviation of about 22.1 (e.g. 22.1±10%) (such as e.g. copy number change-point component 7, cp7, in Table 1) and the predetermined threshold is between 1.91e-5 and 1.23e-3, between 1.91e-5 and 1.1e-3 or between 1.035e-3 and 1.23e-3. In embodiments, the distribution C1 is a Gaussian distribution with a mean of about 7.3 (e.g. 7.3±10%) and a standard deviation of about 3.4 (e.g. 3.4±10%) (such as e.g. copy number change-point component 6, cp6, in Table 1) and the predetermined threshold is between 2.8e-4 and 6.6e-3, between 2.8e-4 and 6.6e-3 or between 4.72e-3 and 6.6e-3. In embodiments, the distribution C1 is a Gaussian distribution with a mean of about 3.0 (e.g. 3.0±10%) and a standard deviation of about 1.0 (e.g. 1.0±10%) (such as e.g. copy number change-point component 5, cp5, in Table 1) and the predetermined threshold is between 0.006 and 0.023.

The distribution C2 is preferably a Gaussian distribution, such as a Gaussian distribution with a mean of about 30.9

(e.g. ±10%) and standard deviation of about 23.1 (e.g. ±10%) (such as copy number component 8, cn8, in Table 1) or a Gaussian distribution with a mean of about 8.4 (e.g. ±10%) and standard deviation of 3.5 (e.g. ±10%) (such as copy number component 7, cn7, in Table 1). In embodiments, the predetermined threshold for the segment copy number sum-of-posterior probabilities is between 2e-3 and 1.5e-2 (such as e.g. 0.006882869). In embodiments, the distribution C2 is a Gaussian distribution, such as a Gaussian distribution with a mean of about 30.9 (e.g. ±10%) and standard deviation of about 23.1 (e.g. ±10%) (such as copy number component 8, cn8, in Table 1) and the predetermined threshold is between 7e-5 and 6e-3, between 7e-5 and 1.1e-4, about 1.5e-3 or between 2e-3 and 6e-3. In embodiments, the distribution C2 is a Gaussian distribution with a mean of about 8.4 (e.g. ±10%) and standard deviation of 3.5 (e.g. ±10%) (such as copy number component 7, cn7, in Table 1), and the predetermined threshold is between 0.0017 and 0.017, about 0.0017 or between 0.012 and 0.017.

The distributions C3 and/or C4 are preferably Gaussian distributions. For example, distribution C3 may be a Gaussian distribution with a mean between 400,000 and 2,500,000 and a standard deviation between 150,000 and 800,000 (such as e.g. segment size components 1-3, ss1-ss3, in Table 1). Distribution C4 may for example be a Gaussian distribution with a mean between 15,000,000 and 60,000,000 and a standard deviation between 5,000,000 and 21,000,000 (such as e.g. segment size components 7-9, ss7-ss9 in Table 1). In embodiments, the predetermined threshold for the segment size sum-of-posterior probabilities is between 0.029 and 0.1527743, between 0.029 and 0.033, between 0.032 and 0.033, or about 0.1527743. In embodiments, C3 is a Gaussian distribution with a mean between 400,000 and 800,000 and a standard deviation between 150,000 and 800,000 (such as e.g. segment size component 1, ss1, in Table 1), and the predetermined threshold is between 0.02 and 0.032, such as e.g. 0.032. In embodiments, C3 is a Gaussian distribution with a mean between 800,000 and 1,800,000 and a standard deviation between 150,000 and 800,000 (such as e.g. segment size component 2, ss2, in Table 1), and the predetermined threshold is between 0.032 and 0.033, such as e.g. 0.033. In embodiments, C3 is a Gaussian distribution with a mean between 1,800,000 and 2,500,000 and a standard deviation between 150,000 and 800,000 (such as e.g. segment size component 3, ss3, in Table 1), and the predetermined threshold is between 0.03 and 0.033, such as e.g. 0.033.

In embodiments, C4 is a Gaussian distribution with a mean between 15,000,000 and 25,000,000 and a standard deviation between 5,000,000 and 21,000,000 (such as e.g. segment size component 7, ss7 in Table 1) and the predetermined threshold is between 0.014 and 0.023, such as e.g. 0.014 or 0.023. In embodiments, C4 is a Gaussian distribution with a mean between 25,000,000 and 55,000,000 and a standard deviation between 5,000,000 and 21,000,000 (such as e.g. segment size component 8, ss8 in Table 1) and the predetermined threshold is between 0.029 and 0.031, such as e.g. 0.029 or 0.031.

In embodiments, the predetermined threshold is determined by comparing the sum-of-posterior probabilities for the respective distributions between resistant and sensitive samples in a training cohort and identifying the threshold that results in the highest proportion of samples being correctly identified as resistant and sensitive (i.e. the threshold that maximises the accuracy of a classification using said threshold). In embodiments, the predetermined threshold is determined by comparing the sum-of-posterior probabilities for the respective distributions between resistant and sensitive samples in a training cohort and identifying the threshold that results in the highest proportion of resistant samples being correctly identified as resistant while not wrongly identifying any sensitive sample as resistant (i.e. the threshold that maximises the specificity—true negative rate—of a classification using said threshold while having 100% sensitivity—true positive rate).

In embodiments, the method comprises obtaining a summarised measure that captures the contribution of multiple copy number features, and comparing the summarised measure to a predetermined threshold, wherein the summarised measure being above the predetermined threshold is indicative of the presence of focal amplifications. In some such embodiments, the summarised measure is exposure ($E_i$) to a copy number signature i ($SbC_i$), where $E_i$ is the value that satisfies the equation:

$$PbC \approx E \times SbC \quad \text{(Equation 1)}$$

where:
E is a vector of size n comprising coefficients E1, . . . , n where Ei is the exposure to signature i;
PbC is a vector of size c≥1, preferably 1≤c≤36, each element in the vector representing the sum-of-posterior probabilities of each copy number event in the copy number profile belonging to a component C, where each component C is a distribution of values for a copy number feature;
SbC is a matrix of size c by n, each value representing the weight of a component C in a signature i.

As such, a column in the matrix SbC, denoted $SbC_i$, contains the weight of all components C in signature i. In some such embodiments, the predetermined threshold is E>0, E>0.005, E>0.01, E>0.015, or E>0.02. Preferably, the predetermined threshold is between 0 and 1%. In embodiments, the predetermined threshold for E is obtained by comparing the values of E for resistant and sensitive samples in a training cohort.

A training cohort may comprise samples obtained from or derived from patients (such as e.g. organoids or spheroids). The sensitive/resistant status in relation to the agent may be known (e.g. from clinical trial data) or may be inferred by measuring the sensitivity of the cells in the sample to the agent. For example, this may be performed by determining the IC50 for the agent (using e.g. cell viability as a readout) for each sample in the training cohort, and classifying the n most sensitive samples (lowest IC50) as sensitive, where n may be chosen based on the expected proportion of sensitive samples in the training cohort.

Preferably, equation (1) is solved applying the constraint that $\Sigma_{i=1}^{i=n} E_i = 1$ (i.e. the exposures across all signatures sum to 1).

In embodiments, the components comprise at least a component C1 that is a distribution of copy number change-point values centred around a value between 2 and 32. C1 may be a distribution of copy number change-point values centred between 4 and 30, between 5 and 30, or between 6 and 30. The distribution is preferably a Gaussian distribution, such as a Gaussian distribution with a mean of about 28.7 (e.g. 28.7±10%) and a standard deviation of about 22.1 (e.g. 22.1±10%) (such as e.g. copy number change-point component 7, cp7, in Macintyre et al.), a Gaussian distribution with a mean of about 7.3 (e.g. 7.3±10%) and a standard deviation of about 3.4 (e.g. 3.4±10%) (such as e.g. copy number change-point component 6, cp6, in Macintyre et al.), or a Gaussian distribution with a mean of about 3.0 (e.g. 3.0±10%) and a standard deviation of about 1.0 (e.g.

1.0±10%) (such as e.g. copy number change-point component 5, cp5, in Macintyre et al.). Where a single component is used, any arbitrary non-zero value can be used for the weight of the component, as the coefficients of the SbC vector capture the relative contributions of the components. Therefore, in such embodiments, exposure E can in the simplest case be calculated as the sum-of-posterior probabilities of each event in the copy number profile belonging to the above mentioned distribution. In other words, a weight of 1 may suitably be used for C1.

In embodiments, the components comprise at least one component C2 that is a distribution of copy number values centred around a value between 5 and 34. C2 may be a distribution of copy number values centred around a value between 6 and 34, between 7 and 34, between 6 and 32, between 7 and 32, or between 8 and 32. The distribution is preferably a Gaussian distribution, such as a Gaussian distribution with a mean of about 30.9 (e.g. ±10%) and standard deviation of about 23.1 (e.g. ±10%) (such as copy number component 8, cn8, in Macintyre et al.) or a Gaussian distribution with a mean of about 8.4 (e.g. ±10%) and standard deviation of 3.5 (e.g. ±10%) (such as copy number component 7, cn7, in Macintyre et al.), where the weight of the component C2 relative to that of component C1 is between 2.5 and 0.3 (or between 0.5 and 1.5, such as e.g. about 0.7).]

In embodiments, the components comprise at least one component C3 that is a distribution of segment sizes centred around a value between 100,000 and 4,000,000 base pairs and at least one component C4 that is a distribution of segment sizes centred around a value between 12,000,000 and 80,000,000 bp. C3 may be a distribution of segment sizes centred around a value between 200,000 and 4,000,000 bp, between 300,000 and 4,000,000 bp, between 400,000 and 4,000,000 bp, between 100,000 and 3,000,000 bp, between 200,000 and 3,000,000 bp, between 300,000 and 3,000,000 bp, between 400,000 and 3,000,000 bp, between 100,000 and 2,500,000 bp, between 200,000 and 2,500,000 bp, between 300,000 and 2,500,000 bp or between 400,000 and 2,500,000 bp. C4 may be a distribution of segment sizes centred around a value between 15,000,000 and 60,000,000. Preferably, components C3 and/or C4 are Gaussian distributions. For example, component C3 may be a Gaussian distribution with a mean between 400,000 and 2,500,000 and a standard deviation between 150,000 and 800,000 (such as e.g. segment size components 1-3, ss1-ss3, in Macintyre et al.). Component C4 may for example be a Gaussian distribution with a mean between 15,000,000 and 60,000,000 and a standard deviation between 5,000,000 and 21,000,000 (such as e.g. segment size components 7-9, ss7-ss9 in Macintyre et al.). The weight of the component C3 relative to that of component C1 may be between 3.5 and 0.1 (preferably between 3.5 and 0.5, or between 0.5 and 2.5, such as e.g. about 1). The weight of the component C4 relative to that of component C1 may be between 1 and 0.1 (preferably between 1 and 0.2, such as e.g. about 0.3). In embodiments, the components consist of one or a plurality of components C1. In embodiments, the components comprises one or more components C1, and one or more components C2. In embodiments, the components comprise one or more components C1, one or more components C3 and one or more components C4. In embodiments, the components consist of one or more components C1, one or more components C2, one or more components C3 and one or more components C4. In embodiments, the components comprise one or more components C1, one or more components C2, one or more components C3 and one or more components C4.

In embodiments, the components comprise up to 7 components that are distributions of copy number change-point values, all of which may be Gaussian distributions. In embodiments, the components comprise up to 8 components that are distributions of copy number values, all of which may be Gaussian distributions. In embodiments, the components comprise up to 10 components that are distributions of segment sizes, all of which may be Gaussian distributions. In embodiments, the components further comprise one or more components that are distributions of breakpoint count per x MB (where x is e.g. 10) values, where each such distribution may be a Poisson distribution. In embodiments, the components comprise up to 3 components that are distributions of breakpoint count per x MB, all of which may be Poisson distributions. In embodiments, the components further comprise one or more components that are distributions of lengths of segment with oscillating copy number, where each such distribution may be a Poisson distribution. In embodiments, the components comprise up to 3 components that are distributions of lengths of segment with oscillating copy number, all of which may be Poisson distributions. In embodiments, the components further comprise one or more components that are distributions of breakpoint count per chromosome arm, where each such distribution may be a Poisson distribution. In embodiments, the components comprise up to 5 components that are distributions of breakpoint count per chromosome arm, all of which may be Poisson distributions. In embodiments, the components comprise components 1 to 36 in Table 1, or distributions with mean (or $\lambda$) and/or standard deviations within 10%, within 5%, within 2% or within 1% of the distribution parameters in Table 1. The corresponding elements of SbC for each component may be the corresponding weights defined in Table 1, or weights within 10%, within 5%, within 2% or within 1% of the weights in Table 1. The components may comprise components 1 to 36 in Table 1 and the corresponding elements of SbC may be the corresponding weights defined in Table 1. The components may consist of components 1 to 36 in Table 1 and the corresponding elements of SbC may be the corresponding weights defined in Table 1. The components may comprise components 1 to 36 in Table 1, or distributions with mean (or $\lambda$) and/or standard deviations within 10%, within 5%, within 2% or within 1% of the distribution parameters in Table 1, and the corresponding elements of SbCi for each component may be the corresponding weights defined in Table 1, or weights within 10%, within 5%, within 2% or within 1% of the weights in Table 1, and wherein SbC further comprises the weights for the additional signatures defined in Table 2, or weights within 10%, within 5%, within 2% or within 1% of the weights in Table 2.

Exposure to signature i may advantageously be calculated using all 7 signatures in Tables 1 and 2, or corresponding signatures, and the exposure Ei that is indicative of the presence of focal amplifications is that of Table 1 (signature 6). In some such embodiments, the patient is an ovarian cancer patient and the agent is an anthracycline, preferably doxorubicin. Signatures corresponding to those in Tables 1 and 2 may be signatures that are obtained by applying the method described in Macintyre et al. (2018) to a different set of copy number profiles, and identifying the signatures obtained through this process that have the closest pattern of contribution of components to signatures in Macintyre et al. (2018) (Tables 1 and 2 below).

In a second aspect, the present invention provides a method for predicting the response of a cancer patient, such as an ovarian cancer patient, to a treatment with a DNA intercalating agent, preferably an anthracycline such as doxorubicin, the method comprising:
(a) obtaining a tumour copy number profile for the patient; and
(b) analysing the copy number profile by:
quantifying, for each copy number event in the copy number profile, a plurality of copy number features;
obtaining a summarised measure that captures the contribution of the plurality of copy number features; and
comparing the summarised measure to a predetermined threshold, wherein the patient is predicted to be resistant to the treatment if the summarised measure is above the predetermined threshold; wherein the summarised measure is exposure ($E_i$) to a copy number signature i ($SbC_i$), where $E_i$ is the value that satisfies the equation:

$$PbC \approx E \times SbC \qquad \text{(Equation 1)}$$

where:
elements in PbC are the sum-of-posterior probabilities of each copy number event in the copy number profile belonging to a component C, where each component C is a distribution of values for a copy number feature as defined in Table 1;
elements in SbC are the weights of each component C in the signature as defined in Tables 1 and 2, and $E_i$ is the exposure to the signature with weights defined in Table 1 (signature 6).

In a third aspect, the present invention provides a method for predicting the response of a cancer patient to a treatment, comprising:
sequencing DNA obtained from the patient to provide a whole genome sequence of the tumour of the patient;
obtaining a tumour copy number profile for the patient from the whole genome sequence of the tumour; and
performing the method of the first or second aspect of the invention using the tumour copy number profile thus obtained.

In some embodiments sequencing comprises extracting and/or amplifying DNA from the sample. The sample may be a tumour tissue sample or a liquid biopsy sample comprising circulating tumour DNA (ctDNA), such as e.g. a blood or plasma sample.

In some cases, the sequencing step may comprise Next-generation Sequencing (NGS), including Illumina™ sequencing, or Sanger sequencing. NGS offers the speed and accuracy required to detect mutations, e.g. through whole-genome sequencing (WGS). Examples of NGS techniques include methods employing sequencing by synthesis, sequencing by hybridisation, sequencing by ligation, pyrosequencing, nanopore sequencing, or electrochemical sequencing. In some embodiments, the sequencing is whole genome sequencing. Advantageously, the sequencing may be shallow whole genome sequencing. For example, shallow whole genome sequencing with a depth of at least 2.5 million reads, preferably at least 2.7 million reads may be used. In embodiments, the sequencing depth to be used is determined using the method described in Macintyre et al. (Trends Genet. 2016 September; 32(9):530-542. doi: 10.1016/j.tig.2016.07.002.), which is incorporated herein by reference. The present inventors have found that shallow whole genome sequencing, especially when the depth of sequencing as adapted to the expected ploidy and purity of the sample, is sufficient to detect copy number changes with enough power to perform the methods of the invention.

In some cases, the method of this aspect of the present invention further comprises a step, prior to sequencing, of preparing a DNA library from a sample (e.g. a tumour sample, a blood or plasma sample) obtained from the patient or from more than one patient. Optionally, the library may be barcoded. In some cases, the method of this aspect of the present invention further comprises a step prior to sequencing of obtaining a sample from the patient. For example, a blood sample or tissue biopsy may be collected from a patient who has been diagnosed as having, or being likely to have, a cancer. Additionally or alternatively a sample comprising circulating tumour DNA (ctDNA) (so-called liquid biopsy) may be obtained and used to provide a whole genome of the tumour for somatic mutation calling. A liquid biopsy approach may be preferred where a tissue biopsy is considered too invasive or where the location of the tumour is unknown or wherein the tumour is only suspected or in the context of tumour monitoring, including after surgical resection. The sample may be subjected to one or more extraction or purification steps, such as centrifugation, in order to obtain substantially cell-free DNA source (e.g. to obtain a plasma sample). It is specifically contemplated that the sample may be transported and/or stored (optionally after freezing). The sample collection may take place at a location remote from the sequencing location and/or the computer-implemented method steps may take place at a location remote from the sample collection location and/or remote from the sequencing location (e.g. the computer-implemented method steps may be performed by means of a networked computer, such as by means of a "cloud" provider). Nevertheless, the entire method may in some cases be performed at single location, which may be advantageous for "on-site" classification or monitoring of cancer.

According to a fourth aspect, there is provided a system for predicting the treatment response of a cancer patient, comprising:
at least one processor; and
at least one non-transitory computer readable medium containing instructions that, when executed by the at least one processor, cause the at least one processor to perform operations comprising:
(a) obtaining a tumour copy number profile for the patient; and
(b) analysing the copy number profile to assess whether the characteristics at least one copy number feature are indicative of the presence of focal amplifications in the tumour genome, wherein the at least one copy number feature is selected from: copy number change-point, segment size and segment copy number; and
(c) predicting that the patient is likely to be resistant to treatment with an agent that induces the formation of micronuclei if the characteristics of the at least one copy number features are indicative of the presence of focal amplifications in the tumour genome. In embodiments, the instructions, when executed by the at least one processor, cause the at least one processor to: receive a whole genome sequence of the patient's tumour and compute a copy number profile from the whole genome sequence of the tumour In some embodiments, the system is for use in the method of the first or second aspect of the invention.

In a fifth aspect, the present invention provides a non-transitory computer readable medium for predicting the treatment response of a cancer patient, comprising instructions that, when executed by at least one processor, cause the at least one processor to perform operations comprising:
(a) obtaining a tumour copy number profile for the patient; and
(b) analysing the copy number profile to assess whether the characteristics at least one copy number feature are indicative of the presence of focal amplifications in the tumour genome, wherein the at least one copy number feature is selected from: copy number change-point, segment size and segment copy number; and
(c) predicting that the patient is likely to be resistant to treatment with an agent that induces the formation of micronuclei if the characteristics of the at least one copy number features are indicative of the presence of focal amplifications in the tumour genome. In some embodiments, the medium is for use in the method of the first or second aspect of the invention.

In a sixth aspect, the present invention provides a method for predicting that a tumour of a patient is resistant to an anthracycline such as doxorubicin, comprising: performing the method of the first aspect of the invention, wherein the tumour is predicted to be resistant if the characteristics of the at least one copy number features are indicative of the presence of focal amplifications in the tumour genome. Preferably, the characteristics of the at least one copy number features is exposure (E) to a copy number signature as described herein, wherein the characteristics are considered indicative of the presence of focal amplifications in the tumour genome if the exposure E is above a threshold. For example, a threshold E>0, E>0.01, E>0.02, or E>0.023. As described in detail herein, exposure to a copy number signature as described herein provides a reliable indication that the tumour is resistant to anthracyclines, and in particular doxorubicin.

In a seventh aspect the present invention provides a method for predicting whether a tumour-burdened patient will benefit from therapy with a DNA intercalating agent such as an anthracycline, preferably doxorubicin, comprising: performing the method of the first or second aspect of the invention, and wherein the patient will not benefit from the therapy if the characteristics of the at least one copy number features are indicative of the presence of focal amplifications in the tumour genome.

According to embodiments of any aspect of the invention, if the characteristics of the at least one copy number features are not indicative of the presence of focal amplifications in the tumour genome, the patient/tumour is predicted to be sensitive to the therapy. Restricting treatment with DNA-intercalation therapy (e.g. anthracycline, preferably doxorubicin therapy) to those cancer patients predicted to be sensitive to such therapy would focus the therapy on those most likely to benefit from it and would spare those patients unlikely to benefit from such therapy, e.g., would spare likely non-responders from undesirable side effects associated with DNA-intercalation therapy.

Once a patient/tumour has been predicted to be sensitive to the therapy, the method of the invention may further comprise:
selecting the patient for treatment with the therapy; and/or
administering a therapeutically effective amount of the therapy to the patient to treat the tumour. When a patient/tumour has been predicted to be resistant to the therapy, the method of the invention may further comprise:
selecting the patient for treatment with another therapy; and/or
administering a therapeutically effective amount of another therapy to the patient to treat the tumour.

The other therapy may be for example paclitaxel. Paclitaxel is commonly administered to ovarian cancer patients in the UK.

Embodiments of the present invention will now be described by way of examples and not limited thereby, with reference to the accompanying figures. However, various further aspects and embodiments of the present invention will be apparent to those skilled in the art in view of the present disclosure.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
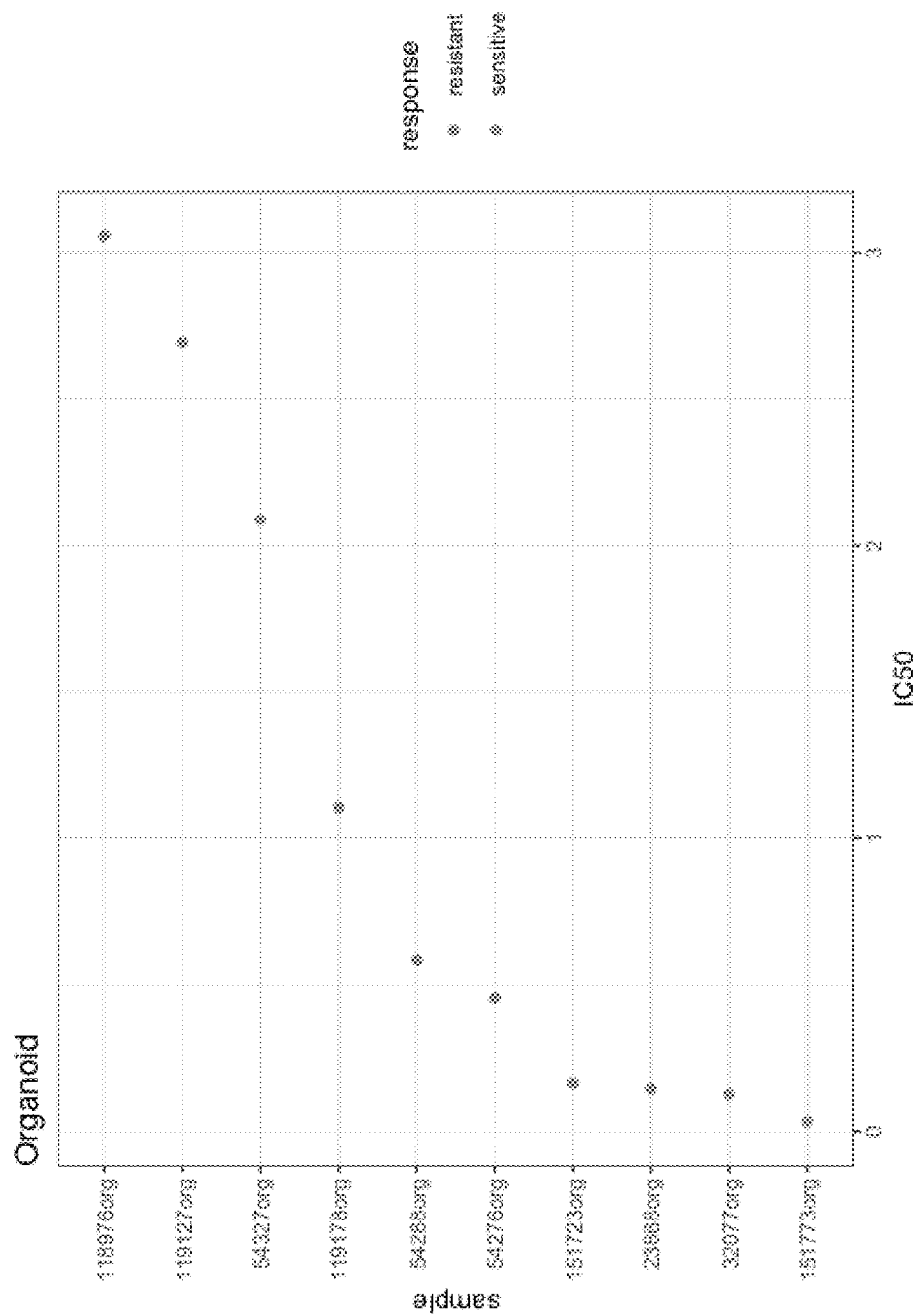
FIG. 1. Doxorubicin response in primary ovarian cancer organoids: IC50 (the drug concentration which induces a 50% reduction in cell viability, x axis, scale=10 µM) for 10 primary ovarian cancer organoids treated with doxorubicin. Each point shows the average of three technical replicates. The two organoids with lowest IC50 were deemed sensitive based on the predicted sensitivity rate to doxorubicin in the patient population from which the organoids were derived.

In describing the present invention, the following terms will be employed, and are intended to be defined as indicated below.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Computer-implemented method" where used herein is to be taken as meaning a method whose implementation involves the use of a computer, computer network or other programmable apparatus, wherein one or more features of the method are realised wholly or partly by means of a computer program.

"Patient" as used herein in accordance with any aspect of the present invention is intended to be equivalent to "subject" and specifically includes both healthy individuals and individuals having a disease or disorder (e.g. a proliferative disorder such as a cancer). The patient may be a human, a companion animal (e.g. a dog or cat), a laboratory animal (e.g. a mouse, rat, rabbit, pig or non-human primate), an animal having a xenografted or xenotransplanted tumour or tumour tissue (e.g. from a human tumour), a domestic or farm animal (e.g. a pig, cow, horse or sheep). Preferably, the patient is a human patient. In some cases, the patient is a human patient who has been diagnosed with, is suspected of having or has been classified as at risk of developing, a cancer.

A "sample" as used herein may be a biological sample, such as a cell-free DNA sample, a cell (including a circulating tumour cell) or tissue sample (e.g. a biopsy), a biological fluid, or an extract (e.g. a DNA extract obtained from the subject). In particular, the sample may be a tumour sample, a biological fluid sample containing DNA or cells, a blood sample (including plasma or serum sample), a urine sample, a cervical smear, an ascites fluid sample. It has been found that urine, ascites fluid and cervical smears contains cells, and so may provide a suitable sample for use in accordance with the present invention. Other sample types suitable for use in accordance with the present invention include fine needle aspirates, lymph nodes samples (e.g. aspirates or biopsies), surgical margins, bone marrow or other tissue from a tumour microenvironment, where traces of tumour DNA may be found or expected to be found. The sample may be one which has been freshly obtained from the subject (e.g. a blood draw) or may be one which has been processed and/or stored prior to making a determination (e.g. frozen, fixed or subjected to one or more purification, enrichment or extractions steps, including centrifugation). For example, the sample may be a formalin-fixed tumour sample. The sample may be derived from one or more of the above biological samples via a process of enrichment or amplification. For example, the sample may comprise a DNA library generated from the biological sample and may optionally be a barcoded or otherwise tagged DNA library. A plurality of samples may be taken from a single patient, e.g. serially during a course of treatment. Moreover, a plurality of samples may be taken from a plurality of patients. In embodiments, the sample is a sample comprising tumour cells. Preferably, such a sample has a tumour purity (where tumour purity can be quantified as the proportion of cells in the sample that are tumour cells) of at least 30%, at least 35%, at least 40%, at least 45%, or at least 50%. Advantageously, the sample has a tumour purity of at least 40%. Without wishing to be bound by theory, it is believed that the copy number profiles generated from samples that have lower tumour purity may be less suitable for the purpose of the present invention as the signal corresponding to the tumour genome may be lost amongst the signal from the genomes of other cells.

A "copy number profile" refers to the quantification of the number of copies for each of a plurality of portions of a genomic sequence. In the context of the present disclosure, a copy number profile is preferably a genome-wide copy number profile. A copy number profile is typically obtained by sequencing a sample of genomic DNA (or a DNA library derived therefrom, as explained above, including a sample of DNA derived from genomic DNA by fragmentation, such as e.g. cell free DNA), and quantifying the number of copies per portion (e.g. per bin, where a bin can be e.g. a 30 kb region) of the genomic sequence, as known in the art. A copy number event refers to a segment of genome that has a copy number associated with it, where the copy number associated with a segment differs from the copy number associated with its immediate neighbouring segment(s). The copy number associated with a segment may differ from the copy number associated with its immediate neighbouring segment(s) because the segment(s) that surround the segment are associated with a different copy number, because the segment(s) that surround the segment are not associated with a copy number (e.g. because data for the segment(s) is missing, or of insufficient quality), or a combination of both (e.g. a segment may be surrounded by a segment that is associated with a different copy number on one side, and a segment that is not associated with a copy number on the other side). In other words, copy number events refer to the longest continuous segments of a copy number profile that are each associated with a single copy number. For this reason, copy number events are also referred to herein as "segments". In embodiments, the copy number profiles comprise at most 350 segments (copy number events), at most 300 segments, or at most 250 segments. Preferably, the copy number profiles comprise at most 250 segments (copy number events). These numbers may be particularly useful when looking at human genome wide copy number profiles. Without wishing to be bound by theory, it is believed that higher numbers of segments may be indicative of unwanted DNA degradation (such as e.g. formalin-mediated DNA degradation).

A "tumour copy number profile" refers to a copy number profile that is associated with a tumour genome. A tumour copy number profile may be obtained by sequencing a sample of genomic DNA (or a DNA library derived therefrom, as explained above, or a sample of DNA derived from genomic DNA by fragmentation) that is derived primarily from tumour cells or assumed to be derived primarily from tumour cells.

As the skilled person understands, such samples can be contaminated with non-tumour DNA, which contamination can be minimised through processing of the sample or of the sequencing data, as known in the art. Preferably, a tumour copy number profile is a copy number profile that has been obtained by sequencing a sample of genomic DNA derived from tumour cells. In other words, a tumour copy number profile is preferably obtained using a sample comprising tumour cells.

The present inventors have discovered that the presence of genome-wide characteristics of copy number features associated with focal amplifications in cancers is an indicator of likely resistance to chemotherapies that induce the formation of micronuclei.

Copy Number Features

Copy number (CN) features are properties of copy number events observable in a copy number profile. Copy number features may include: segment size (the length of each genome segment in a copy number profile), breakpoint count per x MB (the number of genome breaks appearing a sliding windows across the copy number profile, where the window is preferably 10 MB and the copy number profile is preferably genome-wide), change-point copy number (the absolute difference in copy number between adjacent segments in the copy number profile), segment copy number (the observed absolute copy number state of each segment, also referred to herein as "copy number" or "absolute copy number"), breakpoint count per chromosome arm (the number of breaks occurring per chromosome arm), and length of segments with oscillating copy number (number of continuous segments alternating between two copy number states, rounded to the nearest integer copy-number state).

CN features can be observed on a genome-wide basis for a sample or collection of samples. In the context of the present disclosure, the term "genome-wide" refers to the assessment of a feature over a copy number profile that represents a substantial portion of a genome. For example, a substantial portion of a genome may comprise or consist of a chromosome, a plurality of chromosomes, or a portion of a genome determined by the parameters of the sequencing process used such as e.g. sequencing depth. Indeed, as the skilled person understands, even whole genome sequencing protocols may fail to accurately capture every sequence in a genome, especially at lower sequencing depths.

Copy number features that may be characterised on a genome-wide basis, and which can have characteristics that may be used as an indication of the presence of focal amplifications are thought to include one or more of: segment copy number (where high segment copy numbers such as e.g. copy numbers above 5, may be indicative of the presence of focal amplifications), copy number change-points (where the presence of high copy number change-points such as e.g. copy number change-points above 2, preferably above 4, may be associated with the presence of focal amplifications), and segment sizes (where the combined presence of small and large sizes segments, such as e.g. segment sizes below 4,000,000 bp and above 12,000,000 bp, may be indicative of the presence of focal amplifications). A particularly advantageous feature that may be used as an indication of the presence of focal amplifications is the presence of high copy number change-points.

The genome wide characteristics of a copy number feature can be assessed by quantifying the copy number feature for each copy number event in a copy number profile, and obtaining one or more summarised measure for the copy number profile. One or more summarised measure may be obtained for each copy number feature. Alternatively, one or more summarised measure may be obtained which captures the contribution of multiple features. One such measure is exposure to a signature representing the genome-wide imprint of distinct putative mutational processes, for example exposure to a signature described in Macintyre et al. (Nat Genet. 2018 September; 50(9):1262-1270), which is incorporated herein by reference. In particular, exposure to signature 6 as disclosed in Macintyre et al. (2018), and as further explained below, may be computed as a single measure that is indicative of the presence of focal amplification.

As described in Alexandrov et al. (Cell Rep. 2013 Jan. 31; 3(1):246-59. doi: 10.1016/j.celrep.2012.12.008.), exposure to a mutational signature represents the number of mutations attributed to that signature in a particular genome. The signature of a mutational process is the probabilities of a mutational process causing each of the possible mutation types in a mutation catalogue. In Macintyre et al. (2018), the mutation types in the mutational catalogue were defined as individual components of mixture models fitted to the distribution of values obtained for each of 6 copy number features across a set genome-wide copy number profiles from a HGSOC cohort. Copy number signatures (i.e. signatures of copy number alteration processes) were obtained using these, which capture the probability of copy number alteration processes causing copy number events that are distributed according to each of the copy number feature components. Exposure in this context captured the strength of evidence for the presence of copy number alteration events attributable to the signature. Signature 6 as described in Macintyre et al. (2018) is thought to be associated with a mutational process that results in focal amplifications, which manifest themselves by important contributions of copy number feature components capturing high copy number change-points, high copy numbers and both small and large segment sizes. Focal amplifications are copy number aberrations of limited size. For example, focal amplifications may involve regions ≤3 Mb.

Copy number signature 6 was obtained as detailed in Macintyre et al., Nat Genet. 2018 September; 50(9):1262-1270. Briefly, 6 copy number features (segment size, breakpoint count per 10 MB, change-point copy number, segment copy number, breakpoint count per chromosome arm, and length of segments with oscillating copy number, as above) were calculated for 91 samples in the BriTROC-1 HGSOC cohort. Mixture modelling was applied (using the FlexMix V2 package in R) to separate the copy-number feature distributions from all samples into mixtures of Poisson or Gaussian. For distributions representing segment-size, change-point copy-number, and segment copy-number, mixtures of Gaussians were used. For distributions representing breakpoint count per 10 MB, length of segments with oscillating copy-number, and breakpoint count per chromosome arm, mixtures of Poissons were used. This resulted in a total of 36 mixture components.

For each copy-number event, the posterior probability of belonging to a component was computed. For each sample, these posterior event vectors were summed, resulting in a sum-of-posterior probabilities vector. All sum-of-posterior vectors were combined in a patient-by-component sum-of-posterior probabilities matrix. To identify copy-number signatures, this matrix was subjected to non-negative matrix factorization (NMF) using the NMF package in R, with the Brunet algorithm specification. This allowed deconvolution of the patient-by-component sum-of-posteriors matrix into a patient-by-signature matrix and a signature-by-component matrix, identifying seven CN signatures, as well as their defining features (as indicated by the coefficients of the signature-by-component matrix) and exposures (coefficients of the patient-by-signature matrix) in each sample.

The component weights identified by NMF indicated which pattern of global or local copy-number change defined each signature. CN signature 6 showed extremely high copy-number states and high copy-number changepoints from small high copy-number segments interspersed among larger, lower-copy segments. This suggests a mutational process resulting in focal amplification.

Exposure to a copy number signature can be calculated for new samples (i.e. samples other than those used to derive the signatures) as described in Macintyre et al. (2018). In particular, copy number signature exposure can be calculated by:

calculating the coefficients of the patient by component vector (PbC) for a particular sample or the PbC matrix for each of a set of samples, where the coefficients of the PbC vector for a particular sample can be calculate as the sum-of-posterior probabilities of each copy number event belonging to a component (i.e. for each component and each sample, this is the sum, across all events for the sample, of the posterior probability of the event belonging to the component); and performing matrix decomposition to identify the value (or vector of values) that satisfies the equation: $PbC \approx PbS \times SbC$ (or, in practice $PbC = PbS \times SbC + \varepsilon$, where $\varepsilon$ is a residual term to be minimised), where SbC is the row of the signature-by-component matrix that corresponds to signature 6, and PbS is the patient-by-signature value (or vector of values).

Exposure to multiple copy number signatures, such as e.g. any of signatures 1 to 7 of Macintyre et al. (2018), or corresponding signatures identifying by applying the process described in Macintyre et al. (2018) (as described above) to a different set of tumour samples (copy number profiles), can be calculated using the corresponding rows of the signature-by-component matrix. In embodiments, copy number signature exposure is calculated using the LCD function in the YAPSA package in Bioconductor (rdrr.io/bioc/YAPSA/f/README.md). As the skilled person understands, applying the method described in Macintyre et al. (2018) to a different set of copy number profiles (e.g. from samples from a different cohort, which may or may not include some or all of the copy number profiles used in Macintyre et al. (2018)) may result in different values of the signature-by-component matrix. However, without wishing to be bound by theory, it is believed that as the signatures of Macintyre et al. (2018) reflect underlying biological processes that operate in tumours. As such, although the particular values of the signature-by-component matrix may differ, such a process would be expected to identify signatures that can be matched to the signatures of Macintyre et al. (2018) (including at least signature 6), in terms of their patterns of contributions of copy number feature components. This correspondence is likely to be particularly apparent when the method is applied to copy number profiles from ovarian cancer samples. Therefore, signatures corresponding to the signatures in Macintyre et al. (2018) refer to signatures that were identified using the process described above to a set of copy number profiles, preferably from ovarian cancer samples, using a set of copy number features as described herein, and preferably using a set of components as described herein.

In embodiments, exposure (E) to a copy number signature as described herein, such as signature 6 or a simplified version of signature 6 as disclosed in Macintyre et al. (2018), is used as a single measure that is indicative of the presence of focal amplification in a particular copy number profile, where exposure to the copy number signature i (from a set of n signatures, where n can be e.g. 7, where the signatures can include any or all of the signatures disclosed in Macintyre et al. (2018) or corresponding signatures) is the value $E_i$ that satisfies the equation:

$$PbC \approx E \times SbC \qquad \text{(Equation 1)}$$

where:

E is a vector of size n comprising coefficients $E_1, \ldots, n$ where $E_i$ is the exposure to signature i;

PbC is a vector of size c between 1 and 36, each value representing the sum-of-posterior probabilities of each copy number event in the copy number profile belonging to a component C, where each component C is a distribution of values for a copy number feature;

SbC is a matrix of size c by n, where c is between 1 and 36, each value representing the weight of a component C in a copy number signature i as described herein.

Preferably, exposure to signature i (Ei) is calculated using all 7 signatures in Macintyre et al. (2018), or corresponding signatures, and the exposure Ei that is indicative of the presence of focal amplifications is that of signature 6 in Macintyre et al. (2018), or a corresponding signature. In particular, in advantageous embodiments, n=7 and each of the 7 signatures corresponds to a signature in Macintyre et al., (2018) (i.e. it is either identical or obtained through the process described herein, using components as described herein (which may be a subset of the components in Macintyre et al., (2018) and/or may have slightly different parameters due to the particular set of samples to which the distributions of copy number features were fitted), where corresponding signatures can be identified by their similar patterns of contributions of components).

For example, corresponding signatures may be identified by:

(i) quantifying copy number features for a set of tumour copy number profiles (preferably wherein the tumour copy number profiles are from ovarian tumour cells), wherein the features are segment size, breakpoint count per x MB (preferably 10 MB), change-point copy number, segment copy number, breakpoint count per chromosome arm, and length of segments with oscillating copy number;

(ii) identifying mixtures of statistical distributions that fit the distribution of each of these features across all copy number profiles, preferably wherein the statistical distributions are Gaussian distributions for segment-size, change-point copy-number, and segment copy-number, and Poisson distributions for breakpoint count per x MB, length of segments with oscillating copy-number, and breakpoint count per chromosome arm, preferably wherein the number of distributions fitted for each feature are: 7 distributions for copy number change-point, 8 distributions for copy number, 10 distributions for segment size, 3 distributions for breakpoint count per x MB, 5 distributions for breakpoint count per chromosome arm, and 3 distributions for oscillating length;

(iii) for each copy number event in each copy number profile, computing the posterior probability of belonging to each of the distributions identified in step (ii);

(iv) summing the values in (iii) for each component, per copy number profile (i.e. one value per component per copy number profile);

(v) applying non-negative matrix factorization (NMF) to the matrix obtained as a result of step (iv), to obtain a vector of exposures to a set of signatures and a matrix of weights for each distribution (also referred to herein as "component") and signature. Signatures corresponding to those in Tables 1 and 2 can be identified as those signatures obtained in step (v) that show a similar pattern of contribution of the components by: establishing a correspondence between the components in Table 1 and the components identified in step (ii) (where not all components in Table 1 may have a corresponding component in step (ii) and vice-versa; and comparing the weights obtained in step (v) to the weights for the corresponding components in Tables 1 and 2, based on those components that were found to have a corresponding component. For example, if the components identified in step (ii) comprise fewer than 36 components, some or all of which could be matched to one of the 36 components in Table 1, then only the weights corresponding to these matched components in Tables 1 and 2 may be used. Similarly, if the components identified in step (ii) comprise more than 36 components, only the weights in Tables 1 and 2 for components that could be matched to a component identified in step (ii) may be used.

Preferably, equation (1) is solved applying the constraint that $\sum_{i=1}^{i=n} E_i = 1$ (i.e. the exposures across all signatures sum to 1).

In embodiments, a copy number profile is considered to show evidence of exposure to a signature i if the exposure $E_i$ is above a threshold. The threshold may be predetermined, such as e.g. 0, 0.005 (0.5%), 0.01 (1%), etc. Preferably, the threshold is between 0 and 1% (i.e. 0 and 0.01). In embodiments, the threshold may be determined by comparison between exposure values in samples from patients with different phenotypes. For example, a threshold may be determined by calculating the exposure to signature i ($E_i$) for one or more patients that are sensitive to a drug, calculating the exposure to signature i ($E_i$) for one or more patients that are resistant to a drug, and identifying a level of exposure that adequately classifies patients as sensitive or resistant. Whether a classification is adequate may depend on multiple parameters, such as e.g. the treatment options envisaged. Advantageously, the threshold level of exposure may be identified as the value of exposure such that all sensitive patients are below the threshold. This may reduce the risk of sensitive patients being classified as resistant and hence not administered a treatment that may have been effective.

The components comprise at least a component C1 that is a distribution of copy number change-point values centred around a value between 2 and 32 (preferably between 4 and 30, between 5 and 30, or between 6 and 30). The distribution is preferably a Gaussian distribution, such as a Gaussian distribution with a mean of about 28.7 (e.g. 28.7±10%) and a standard deviation of about 22.1 (e.g. 22.1±10%) (such as e.g. copy number change-point component 7, cp7, in Macintyre et al.), a Gaussian distribution with a mean of about 7.3 (e.g. 7.3±10%) and a standard deviation of about 3.4 (e.g. 3.4±10%) (such as e.g. copy number change-point component 6, cp6, in Macintyre et al.), or a Gaussian distribution with a mean of about 3.0 (e.g. 3.0±10%) and a standard deviation of about 1.0 (e.g. 1.0±10%) (such as e.g. copy number change-point component 5, cp5, in Macintyre et al.). Where a single component is used, any arbitrary non-zero value can be used for the weight of the component, as the coefficients of the SbC vector capture the relative contributions of the components. Therefore, in such embodiments, exposure E can in the simplest case be calculated as the sum-of-posterior probabilities of each event in the copy number profile belonging to the above mentioned distribution. In other words, a weight of 1 may suitably be used for C1.

In embodiments, the components comprise at least one component C2 that is a distribution of copy number values centred around a value between and 34 (preferably between 6 and 34, between 7 and 34, between 6 and 32, between 7 and 32, or between 8 and 32). The distribution is preferably a Gaussian distribution, such as a Gaussian distribution with a mean of about 30.9 (e.g. ±10%) and standard deviation of about 23.1 (e.g. ±10%) (such as copy number component 8, cn8, in Macintyre et al.) or a Gaussian distribution with a mean of about 8.4 (e.g. ±10%) and standard deviation of 3.5 (e.g. ±10%) (such as copy number component 7, cn7, in Macintyre et al.), where the weight of the component C2 relative to that of component C1 is between 2.5 and 0.3 (or between 0.5 and 1.5, such as e.g. about 0.7).

In embodiments, the components comprise at least one component C3 that is a distribution of segment sizes centred around a value between 100,000 and 4,000,000 base pairs (preferably between 200,000 and 4,000,000 bp, between 300,000 and 4,000,000 bp, between 400,000 and 4,000,000 bp, between 100,000 and 3,000,000 bp, between 200,000 and 3,000,000 bp, between 300,000 and 3,000,000 bp, between 400,000 and 3,000,000 bp, between 100,000 and 2,500,000 bp, between 200,000 and 2,500,000 bp, between 300,000 and 2,500,000 bp or between 400,000 and 2,500,000 bp), and at least one component C4 that is a distribution of segment sizes centred around a value between 12,000,000 and 80,000,000 bp (preferably between 15,000,000 and 60,000,000). Preferably, components C3 and/or C4 are Gaussian distributions. For example, component C3 may be a Gaussian distribution with a mean between 400,000 and 2,500,000 and a standard deviation between 150,000 and 800,000 (such as e.g. segment size components 1-3, ss1-ss3, in Macintyre et al.). Component C4 may for example be a Gaussian distribution with a mean between 15,000,000 and 60,000,000 and a standard deviation between 5,000,000 and 21,000,000 (such as e.g. segment size components 7-9, ss7-ss9 in Macintyre et al.). The weight of the component C3 relative to that of component C1 may be between 3.5 and 0.1 (preferably between 3.5 and 0.5, or between 0.5 and 2.5, such as e.g. about 1). The weight of the component C4 relative to that of component C1 may be between 1 and 0.1 (preferably between 1 and 0.2, such as e.g. about 0.3).

In embodiments, the components consist of one or a plurality of components C1. In embodiments, the components comprises one or more components C1, and one or more components C2. In embodiments, the components comprise one or more components C1, one or more components C3 and one or more components C4. In embodiments, the components comprise one or more components C1, one or more components C2, one or more components C3 and one or more components C4. In embodiments, the components consist of one or more components C1, one or more components C2, one or more components C3 and one or more components C4.

In embodiments, the components comprise 1, 2, 3, 4, 5, 6, 7 or up to 7 components that are distributions of copy number change-point values, all of which may be Gaussian distributions. In embodiments, the components comprise 1, 2, 3, 4, 5, 6, 7, 8 or up to 8 components that are distributions of copy number values, all of which may be Gaussian distributions. In embodiments, the components comprise 1, 2, 3, 4, 5, 6, 7, 8, 9, 10 or up to 10 components that are distributions of segment sizes, all of which may be Gaussian distributions. In embodiments, the components further comprise one or more components that are distributions of breakpoint count per x MB (where x is e.g. 10) values, where each such distribution may be a Poisson distribution. In embodiments, the components comprise up to 3 components that are distributions of breakpoint count per x MB, all of which may be Poisson distributions. In embodiments, the components further comprise one or more components that are distributions of lengths of segment with oscillating copy number, where each such distribution may be a Poisson distribution. In embodiments, the components comprise up to 3 components that are distributions of lengths of segment with oscillating copy number, all of which may be Poisson distributions. In embodiments, the components further comprise one or more components that are distributions of breakpoint count per chromosome arm, where each such distribution may be a Poisson distribution. In embodiments, the components comprise up to 5 components that are distributions of breakpoint count per chromosome arm, all of which may be Poisson distributions.

In embodiments, the components comprise components 1 to 36 defined in Table 1. In embodiments, the components comprise components 1 to 36 defined in Table 1 and the corresponding coefficients in the SbC matrix are the corresponding weights defined in Table 1. In Table 1, N(m, sd) refers to a Gaussian distribution with mean=m and standard deviation=sd, and P(l) is a Poisson distribution with $\lambda$=1. In embodiments, the components comprise components 1 to 36 in Table 1, or distributions with mean (or $\lambda$) and/or standard deviations within 10%, within 5%, within 2% or within 1% of the distribution parameters in Table 1. In some such embodiments, the components have the corresponding weights defined in Table 1, or weights within 10%, within 5%, within 2% or within 1% of the weights in Table 1.

TABLE 1

Components and weights for calculating exposure to the copy number signature according to the present disclosure.

| Component | Type | Macintyre et al. component No | Distribution | Weight |
|---|---|---|---|---|
| | Copy number change-point | cp1 | N (0.49452648, 0.15645341) | 2.220446e−16 |
| | Copy number change-point | cp2 | N (0.96834666, 0.15629395) | 5.227448e+01 |
| | Copy number change-point | cp3 | N (1.17859816, 0.22669911) | 1.844236e+01 |
| | Copy number change-point | cp4 | N (1.82240751, 0.39907792) | 7.093089e−04 |
| C1 | Copy number change-point | cp5 | N (3.00685766, 1.03958107) | 2.256705e+02 |
| C1 | Copy number change-point | cp6 | N (7.3149416, 3.45921997) | 3.407536e+02 |
| C1 | Copy number change-point | cp7 | N (28.7346654, 22.0551593) | 1.094957e+02 |
| | Copy number | cn1 | N (0.99799839, 0.10280125) | 1.796167e−12 |
| | Copy number | cn2 | N (1.98135508, 0.12149214) | 6.025619e+01 |
| | Copy number | cn3 | N (2.56168152, 1.00230467) | 4.030726e+01 |
| | Copy number | cn4 | N (2.99108879, 0.1440896) | 1.377268e+02 |
| | Copy number | cn5 | N (3.97051928, 0.17145688) | 5.498051e+01 |
| | Copy number | cn6 | N (4.27164691, 1.58429331) | 1.601024e+02 |
| C2 | Copy number | cn7 | N (8.39260927, 3.50149434) | 2.473803e+02 |
| C2 | Copy number | cn8 | N (30.8672269, 23.15811) | 1.278820e+02 |
| C3 | Segment size | ss1 | N (426861.918, 186924.872) | 3.664985e+02 |
| C3 | Segment size | ss2 | N (1081858.4, 407302.128) | 2.200091e+02 |
| C3 | Segment size | ss3 | N (2233029.82, 749092.036) | 3.772309e+01 |
| | Segment size | ss4 | N (4303321.09, 1115831.53) | 2.220446e−16 |
| | Segment size | ss5 | N (7304340.04, 1644306.83) | 5.356412e+00 |
| | Segment size | ss6 | N (10479327.2, 2972413.84) | 3.131356e−10 |
| C4 | Segment size | ss7 | N (16419124.1, 5226151.49) | 4.811576e+01 |
| C4 | Segment size | ss8 | N (29508322.4, 9703791.44) | 8.298639e+01 |
| C4 | Segment size | ss9 | N (58638899, 20499001.4) | 9.536135e+01 |
| | Segment size | ss10 | N (118310989, 45210595) | 4.209353e−09 |
| | Breakpoint count per 10 MB | bp1 | P (6.47E−05) | 7.331333e+02 |
| | Breakpoint count per 10 MB | bp2 | P (1.25529082) | 2.952606e+02 |
| | Breakpoint count per 10 MB | bp3 | P (4.07458306) | 5.698965e+01 |
| | Breakpoint count per chromosome arm | ct1 | P (0.06154321) | 2.673626e+01 |
| | Breakpoint count per chromosome arm | ct2 | P (2.62256735) | 5.015466e+01 |
| | Breakpoint count per chromosome arm | ct3 | P (7.77720192) | 7.164583e+01 |

TABLE 1-continued

Components and weights for calculating exposure to the copy number signature according to the present disclosure.

| Component | Type | Macintyre et al. component No | Distribution | Weight |
|---|---|---|---|---|
| | Breakpoint count per chromosome arm | ct4 | P (17.5464903) | 7.987976e+00 |
| | Breakpoint count per chromosome arm | ct5 | P (33.5306827) | 2.220446e−16 |
| | Oscillating CN length | os1 | P (0.33948439) | 4.479586e+02 |
| | Oscillating CN length | os2 | P (2.62714528) | 3.473049e+00 |
| | Oscillating CN length | os3 | P (9.58714514) | 2.220446e−16 |

In embodiments, the components comprise components 1 to 36 defined in Table 1, and exposure to a signature as described herein is calculated as $E_6$ using all 7 signatures Table 2 (where T1 refers to Table 1, and the signature numbering "Sig. 1", etc. corresponds to the numbering in Macintyre et al., (2018)). In such embodiments, the components comprise components 1 to 36 defined in Table 1, the corresponding coefficients for $E_6$ in the SbC matrix are the corresponding weights defined in Table 1, and the corresponding coefficients for $E_{1-5, 7}$ in the SbC matrix are the corresponding weights defined in Table 2. In some such embodiments, the components comprise components 1 to 36 in Table 1, or distributions with mean (or $\lambda$) and/or standard deviations within 10%, within 5%, within 2% or within 1% of the distribution parameters in Table 1. In some such embodiments, the components have the corresponding weights defined in Tables 1 and 2, or weights within 10%, within 5%, within 2% or within 1% of the weights in Tables 1 and 2.

TABLE 2

Weights for calculating exposure to copy number signatures according to the present disclosure.

| Comp. No | Weight Sig. 6 | Weight Sig. 1 | Weight Sig. 2 | Weight Sig. 3 | Weight Sig. 4 | Weight Sig. 5 | Weight Sig. 7 |
|---|---|---|---|---|---|---|---|
| ss1 | see T1 | 5.874998E−09 | 6.357651E+02 | 3.495885E+02 | 3.195265E+02 | 2.758839E+02 | 2.220446E−16 |
| ss2 | see T1 | 3.919165E+01 | 9.344973E+02 | 2.107191E+02 | 5.132767E+02 | 4.911694E+02 | 1.175359E−09 |
| ss3 | see T1 | 8.692671E+00 | 7.997478E+02 | 5.224959E+02 | 2.224959E+02 | 4.837410E+02 | 1.392389E+02 |
| ss4 | see T1 | 1.186716E−12 | 4.102743E+02 | 1.792579E+02 | 2.559155E+02 | 2.224521E+02 | 2.443877E+02 |
| ss5 | see T1 | 9.416554E−04 | 1.399407E+02 | 1.771104E+02 | 1.246349E+02 | 9.130593E+01 | 2.559156E+02 |
| ss6 | see T1 | 1.134795E−02 | 1.056615E+02 | 2.384823E+02 | 1.104778E+02 | 3.804761E+01 | 3.082691E+02 |
| ss7 | see T1 | 2.515102E+01 | 3.263778E+01 | 3.801034E+02 | 1.276619E+02 | 3.035091E+01 | 4.499549E+02 |
| ss8 | see T1 | 2.815465E+02 | 2.220446E−16 | 3.145101E+02 | 7.575488E+01 | 1.659839E−14 | 4.609180E+02 |
| ss9 | see T1 | 4.271319E+02 | 2.220446E−16 | 6.699405E+01 | 7.048058E−01 | 2.220446E−16 | 1.441790E+02 |
| ss10 | see T1 | 2.163535E+02 | 1.208025E−01 | 6.462114E−10 | 2.220446E−16 | 1.884395E+00 | 2.220446E−16 |
| bp1 | see T1 | 5.922842E+03 | 4.201845E+01 | 8.765489E+02 | 1.458561E+02 | 6.562871E+01 | 1.451856E+03 |
| bp2 | see T1 | 1.674698E+03 | 3.217679E+02 | 1.393995E+03 | 5.482652E+02 | 2.328218E+02 | 1.943561E+03 |
| bp3 | see T1 | 5.342843E+00 | 3.403277E+02 | 8.479927E+01 | 1.959023E+02 | 1.740944E+02 | 1.737137E+00 |
| os1 | see T1 | 2.220446E−16 | 6.504749E+02 | 6.404900E+02 | 1.503803E+03 | 1.552809E+03 | 5.291782E+02 |
| os2 | see T1 | 2.220446E−16 | 2.183590E+02 | 9.403746E+01 | 9.638086E+01 | 4.639440E+01 | 6.390338E+01 |
| os3 | see T1 | 2.220446E−16 | 2.485718E+01 | 3.924113E+00 | 4.551777E−02 | 2.220446E−16 | 2.304946E−09 |
| cp1 | see T1 | 2.140049E−06 | 9.986209E−02 | 1.180214E+02 | 2.220446E−16 | 1.720462E+03 | 5.979281E−01 |
| cp2 | see T1 | 8.456386E+01 | 1.750840E+03 | 1.106694E+03 | 2.220446E−16 | 3.713199E−02 | 1.065770E+03 |
| cp3 | see T1 | 6.557840E+01 | 7.026403E+02 | 3.489020E+02 | 2.342685E+02 | 2.220446E−16 | 3.358230E+02 |
| cp4 | see T1 | 9.879969E+01 | 3.949138E+02 | 3.544807E+02 | 1.286606E+03 | 2.220446E−16 | 1.497280E+02 |
| cp5 | see T1 | 2.567242E+01 | 7.040137E+01 | 8.888528E+01 | 6.385500E+02 | 8.912176E+00 | 2.674814E−14 |
| cp6 | see T1 | 6.187037E−01 | 4.608997E+00 | 3.738473E+00 | 3.835558E+01 | 2.578551E+00 | 2.220446E−16 |
| cp7 | see T1 | 2.220446E−16 | 9.290701E−02 | 2.562223E−01 | 2.220446E−16 | 1.192290E−01 | 2.731235E−01 |
| cn1 | see T1 | 2.220446E−16 | 2.220446E−16 | 6.538948E+02 | 2.220446E−16 | 9.459096E+01 | 2.220446E−16 |
| cn2 | see T1 | 1.946635E+02 | 3.112491E+02 | 1.275464E+03 | 2.163790E+01 | 3.566195E+02 | 1.128208E+02 |
| cn3 | see T1 | 2.403932E+02 | 6.226564E+02 | 4.149842E+02 | 2.750706E+02 | 6.783415E+02 | 4.923219E+02 |
| cn4 | see T1 | 1.378518E+02 | 7.158619E+02 | 1.887778E+02 | 4.488714E−01 | 2.763153E+01 | 4.028007E+02 |
| cn5 | see T1 | 4.254641E+01 | 2.016845E+02 | 2.220446E−16 | 1.923032E+02 | 2.220446E−16 | 1.784711E+02 |
| cn6 | see T1 | 1.899706E+02 | 8.976670E+02 | 2.220446E−16 | 1.497681E+03 | 3.677175E+02 | 6.793631E+02 |
| cn7 | see T1 | 1.195794E+01 | 3.100969E+01 | 2.220446E−16 | 3.025158E+02 | 1.618100E+01 | 9.051164E−13 |
| cn8 | see T1 | 2.601461E−01 | 8.277609E+02 | 9.966975E−13 | 8.002977E−01 | 3.491317E−01 | 1.194772E+00 |
| ct1 | see T1 | 5.143919E+02 | 3.071631E+01 | 1.713388E+00 | 2.220446E−16 | 1.311933E+01 | 2.878734E+01 |
| ct2 | see T1 | 6.143409E+02 | 2.220446E−16 | 9.037079E+01 | 5.853353E+00 | 2.220446E−16 | 2.245124E+02 |
| ct3 | see T1 | 1.868481E+01 | 6.673895E−05 | 1.878851E+02 | 6.898058E+01 | 8.387338E+00 | 2.583170E+02 |
| ct4 | see T1 | 2.220446E−16 | 9.513077E+01 | 2.220446E−16 | 2.005521E+01 | 4.124064E+01 | 2.220446E−16 |
| ct5 | see T1 | 2.220446E−16 | 3.569713E+01 | 2.220446E−16 | 3.141504E+00 | 3.494840E+00 | 2.220446E−16 |

Cancers with High Chromosomal Instability

Genomic and chromosomal instability is characterised by the presence of mutations within a genome, including single nucleotide variants, copy number variants (including aneuploidy; also referred to as "copy number alterations"), and/or chromosomal rearrangements (also referred to as structural variation when they concern large portions of the genome such as e.g. >1 kb). Chromosomal instability is characterised by the presence of copy number alterations and chromosomal rearrangements (including structural variants) within a genome. Genomic instability typically refers to the presence of single nucleotide variants within a genome. Most cancers are thought to display some amount of chromosomal instability. However, some cancers are considered to have high chromosomal instability, showing an unusually high frequency of copy number alterations and chromosomal rearrangements within their genomes. In particular, within the context of the present invention, cancers with high chromosomal instability may have a high number of copy number variation events within their genome. A copy number variation event is the presence of a section of the genome at a number of repeats different from the expected number in a wild type genome (i.e. 2 for a diploid organism such as a human). Without wishing to be bound by theory, the present invention is believed to be particularly useful in the context of cancers with high chromosomal instability, as their genomes are more likely to show genome-wide signs of focal amplifications which may be indicative of tolerance to the formation of micronuclei. Cancers with high chromosomal instability include all epithelial cancers (carcinomas), including but not limited to lung cancer, oesophageal cancer, pancreatic cancer, breast cancer, and ovarian cancer, as well as sarcomas and glioblastoma. In embodiments, a sample according to the invention is from a patient who has been diagnosed as having or is likely to have a carcinoma. In embodiments, a sample according to the invention is from a patient who has been diagnosed as having or is likely to have lung cancer, oesophageal cancer, pancreatic cancer, sarcoma, glioblastoma, breast cancer or ovarian cancer. Preferably, the patient has been diagnosed as having or being likely to have ovarian cancer, such as HGSOC. In embodiments, the patient has been diagnosed as having, or being likely to have breast cancer, such as triple negative breast cancer.

It is particularly advantageous for the method of the invention to be used in relation to a patient who has not yet been subjected to therapy with one or more DNA intercalators. Preferably, the patient has not yet been treated with an anthracycline, such as doxorubicin. In embodiments, the subject has not undergone prior chemotherapy. In embodiments, the patients has undergone prior chemotherapy, preferably with agents other than anthracyclines. For example, the patient may have undergone chemotherapy with carboplatin and/or paclitaxel. In embodiments, the patient has undergone debulking surgery. In embodiments, the patient has relapsed or not responded to prior chemotherapy. In embodiments, the patient has been diagnosed as having a cancer that is resistant to platinum-based chemotherapy. In some such embodiments, the patient has not undergone further chemotherapy treatment after being diagnosed as platinum-resistant. For example, a patient may be diagnosed as platinum-resistant if the patient's cancer has relapsed within a specified period (e.g. 6 months) of undergoing platinum-based therapy. In particular, the patient may not have undergone paclitaxel (mono)therapy and/or doxorubicin (mono)therapy after being diagnosed platinum-resistant. In other such embodiments, the patient may have undergone chemotherapy with an agent other than an anthracycline, for example paclitaxel, after being diagnosed platinum-resistant. In other embodiments, the patient has been diagnosed as having a cancer that is sensitive to platinum-based chemotherapy. For example, a patient may be diagnosed as platinum-sensitive if the patient's cancer has not relapsed within a specified period (e.g. 6 months) of undergoing platinum-based therapy. In some such embodiments, the patient may not have undergone platinum-based chemotherapy after being diagnosed as platinum-sensitive.

In embodiments, the patient may be an ovarian cancer patient who is homologous recombination-deficient, such as e.g. a patient that has a somatic or non-somatic BRCA1/2 mutation. Alternatively, the patient may be an ovarian cancer patient who is not homologous recombination-deficient. The patient may not have been identified as having a somatic or non-somatic BRCA1/2 mutation, and/or may be believed to have wild type BRCA1 and BRCA2 genes. Ovarian cancer patients who have been identified as having a BRCA1/2 mutation are thought to be slightly more likely to benefit from doxorubicin therapy. However, for patients whose BRCA1/2 status is unknown or believed to be wild type, there is currently no reliable way to predict whether the patient will benefit from treatment with chemotherapies such as doxorubicin. Such patients stand to benefit the most from the present invention. However, even patients known to have a BRCA1/2 mutation are likely to benefit from the present invention since the predictive power of the presence of the BRCA1/2 mutation is weak.

Therapies

Micronuclei are chromatin-containing bodies that form when a chromosome or fragment of chromosome is not incorporated into the nucleus of either daughter cell during cell division. Micronuclei are believed to be associated with genotoxic events, DNA damage and chromosomal instability. The formation of micronuclei, when it does not cause the death of the cell, is hypothesised to form part of the process of cell transformation (Hintzsche et al., Scientific Reports, (2018)8:3371).

Some chemotherapies are known to induce micronuclei. These include genotoxic therapies, and especially genotoxic chemotherapies, including therapies that act as DNA intercalating agents (such as anthracyclines), therapies that act as spindle poison (such as vinblastine), therapies that stall the replication fork (such as alkylating agents, for example methyl methanesulfonate, MMS), and DNA crosslinkers (such as mytomycin C, MMC) (Hintzsche et al., Scientific Reports, (2018)8:3371). A DNA intercalating agent is a compound that can interact with DNA by insertion between base pairs. Some DNA intercalating agents have been used as chemotherapies in the treatment of cancer, including doxorubicin, daunorubicin and dactinomycin. In particular, DNA intercalating agents that act as topoisomerase-II poison may induce the formation of micronuclei. A topoisomerase-II poison is a compound that blocks the action of topoisomerase-II, preventing it from performing its normal function during the cell cycle. These include anthracyclines such as doxorubicin, daunorubicin, epirubicin and idarubicin. Indeed, there is long standing evidence that anthracyclines can induce micronuclei (see e.g. Bhuyan et al., Cancer Research 43, 5293-5297, 1983). A spindle poison is a compound that disrupts the function of the mitotic spindle. Spindle poisons include vinca alkaloids such as vinblastine. Alkylating agents are compounds that add an alkyl group to the guanine base of the DNA molecule. These include alkyl sulfonates, nitrogen mustards, ethylenimines, nitrosureas and triazines. DNA crosslinkers are agents that react with two DNA nucleotides and form a covalent link between them. DNA crosslinkers include cisplatin, oxaliplatin, mitomycin C, and nitrogen mustards.

Doxorubicin is widely used as anti-cancer chemotherapy, including in the treatment of breast cancer, bladder cancer, sarcomas, lymphomas and leukemia. Doxorubicin is available in liposomal (i.e. liposome-encapsulated) forms, and in non-liposomal forms. Liposomal doxorubicin is available in a pegylated liposome-encapsulated form, commercially known as Doxil. Doxorubicin is also available in a non-pegylated liposomal form, commercially known as Myocet. References to "doxorubicin" in the context of the present disclosure encompasses all forms of doxorubicin. In particular, the term "doxorubicin" explicitly encompasses liposomal (pegylated and non-pegylated) and non-liposomal forms of doxorubin, unless otherwise specified.

The present invention provides methods for predicting whether a cancer patient is likely to respond to a chemotherapy that induces micronuclei, as well as methods for treating patients that have been diagnosed as having or being likely to have a cancer, where the course of treatment can be adapted depending on whether the patient is predicted to be likely to respond to a chemotherapy that induces micronuclei. As such, the step of predicting whether a cancer patient is likely to respond to a chemotherapy may advantageously be performed: (i) in relation to a patient that has not yet undergone any chemotherapy; (ii) in relation to a patient that has not yet undergone chemotherapy with an agent that induces micronuclei; (iii) in relation to a patient that has not yet undergone chemotherapy with an agent that has a DNA intercalation function; (iv) in relation to a patient that has not yet undergone chemotherapy with an anthracycline; and/or (v) in relation to a patient that has not yet undergone chemotherapy with doxorubicin. The methods of treating a patient may comprise treating the patient with an agent that induces micronuclei, preferably a DNA intercalator, advantageously an anthracycline such as doxorubicin, if the patient is predicted as being unlikely to be resistant to the agent. The methods of treating a patient may comprise treating the patient with an agent that does not induce micronuclei, preferably an agent that is not a DNA intercalator (for example, not an anthracycline such as doxorubicin), if the patient is predicted as being likely to be resistant to an agent that induces micronuclei. The methods of treating a patient may comprise treating the patient with an agent that induces micronuclei, preferably a DNA intercalator, advantageously an anthracycline such as doxorubicin, alone or in combination with a further agent, if the patient is predicted as being unlikely to be resistant to the agent. The further agent may be an agent that induces micronuclei, or an agent that does not induce micronuclei.

Further, the step of predicting whether a cancer patient is likely to respond to a chemotherapy may be repeated throughout the course of treatment of a patient. For example, the step may be performed prior to initiating chemotherapy with an agent other than an anthracycline, and after relapse of the patient following the chemotherapy.

In embodiments, the patient is an ovarian cancer patient and the step of predicting is performed prior to subjecting the patient to chemotherapy, for example chemotherapy with carboplatin and paclitaxel, and/or debulking surgery. In embodiments, the patient is an ovarian cancer patient and the step of predicting is performed after relapse of the patient following chemotherapy, for example chemotherapy with carboplatin and paclitaxel, and/or debulking surgery. In some such embodiments, the patient has been diagnosed as being platinum-resistant, and the method of treating the patient comprises: treating the patient with an agent that induces micronuclei (such as an anthracycline, preferably doxorubicin) if the patient is predicted to be unlikely to be resistant to the agent; or treating the patient with a chemotherapy that does not include the agent (for example, paclitaxel monotherapy) if the patient is predicted to be likely to be resistant to the agent. In other embodiments, the patient has been diagnosed as being platinum-sensitive, and the method of treating the patient comprises: treating the patient with an agent that induces micronuclei (such as an anthracycline, preferably doxorubicin) in combination with or subsequent to platinum-based therapy, if the patient is predicted to be unlikely to be resistant to the agent; or treating the patient with a chemotherapy that does not include the agent (for example, cisplatin monotherapy) if the patient is predicted to be likely to be resistant to the agent. In any embodiment described herein, the agent that induces micronuclei (e.g. an anthracycline, such as doxorubicin), may be administered as a monotherapy (i.e. alone) or in combination with one or more other therapies (which may comprise other chemotherapies or other therapy modalities such as e.g. radiotherapy).

"Predicting the response of a cancer patient to a selected treatment" is intended to mean assessing the likelihood that a patient will experience a positive or negative outcome with a particular treatment.

As used herein, "indicative of a positive treatment outcome" refers to an increased likelihood that the patient will experience beneficial results from the selected treatment (e.g. reduction in tumour size, 'good' prognostic outcome, improvement in disease-related symptoms and/or quality of life).

"Indicative of a negative treatment outcome" is intended to mean an increased likelihood that the patient will not receive the aforementioned benefits of a positive treatment outcome.

The following is presented by way of example and is not to be construed as a limitation to the scope of the claims.

EXAMPLES

Overview of the Examples

To test the hypothesis that genome wide copy number features indicative of focal amplifications were associated with resistance to drugs that induce the formation of micronuclei, primary ovarian cancer organoids were treated with doxorubicin and an IC50 reduction in cell viability was used as a response measure. Signature 6 exposure was calculated for each organoid and the expected resistance rate to doxorubicin in the organoid population was used to define a cut-off on exposure. This cut-off was validated using patient derived spheroids from ascites fluid treated with doxorubicin in vitro, where exposure to the signature was found to be associated with resistance to doxorubicin. Finally, retrospective validation in an ovarian cancer clinical study showed that exposure to signature 6 can be used to identify cases that will be resistant to doxorubicin, using both tumour tissue samples and ctDNA samples.

Figure 5:
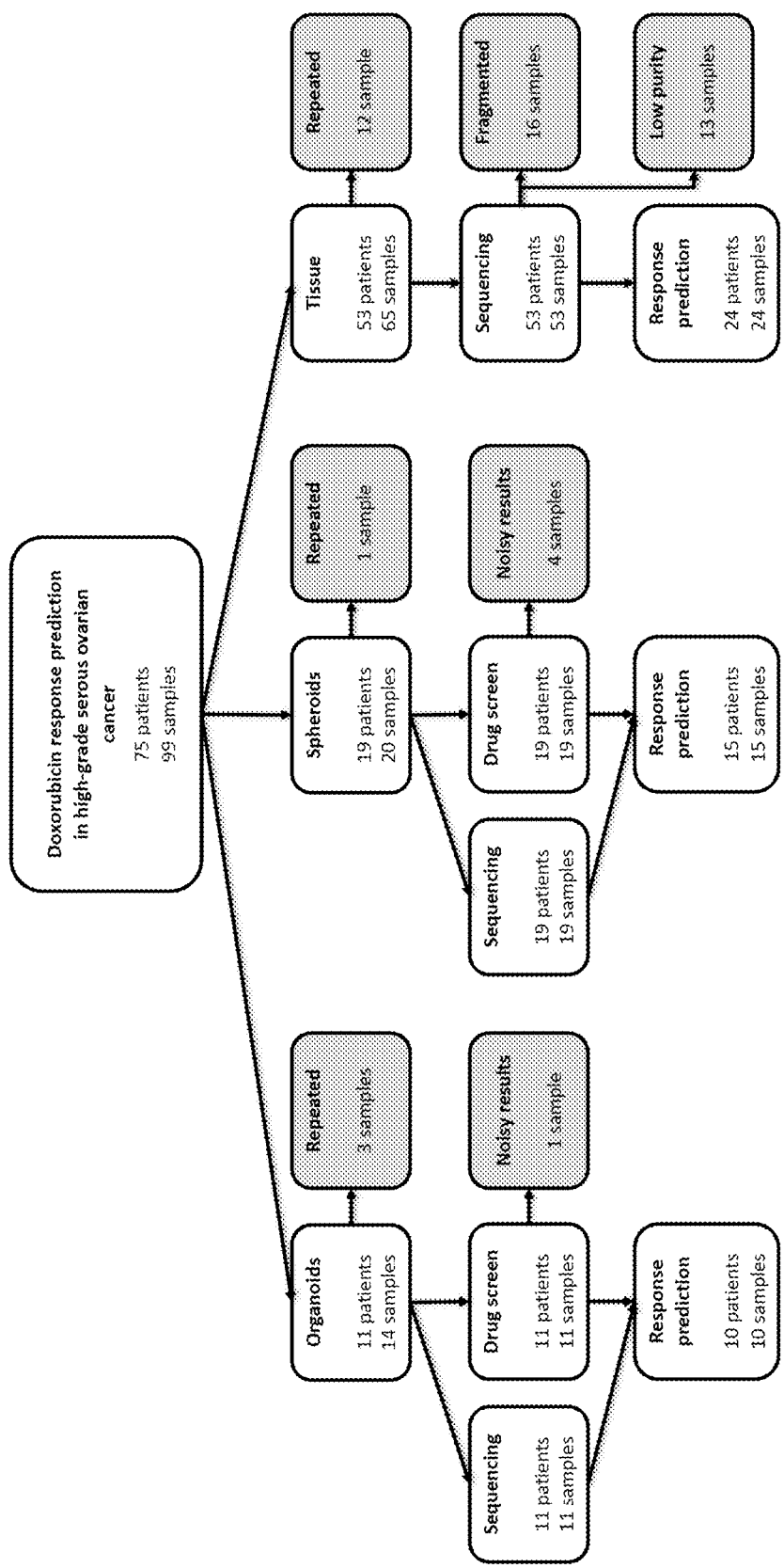
FIG. 5. Sample details and workflow for the analysis in the examples. Primary ovarian cancer organoids were derived from 11 patients. These were (a) sequenced to calculate copy number signature exposure, and (b) treated with doxorubicin to determine the IC50 for each organoid. The expected resistance rate to doxorubicin in the organoid population was used to define a cut-off on exposure to a copy number signature indicative of focal amplifications as described herein (FIG. 1). The cut-off was validated using spheroids derived from ascites fluid samples from 19 patients. Again, the spheroids were (a) sequenced to calculate copy number signature exposure, and (b) treated with doxorubicin in vitro. Exposure to the signature indicative of focal amplifications was found to be associated with resistance to doxorubicin (FIG. 2). This finding was validated using tissue derived data from an ovarian cancer clinical study. Samples from 53 patients were sequenced, and 24 of these were selected for calculation of copy number signature exposure, after quality control. This analysis showed that exposure to a copy number signature indicative of focal amplifications as described herein can be used to identify cases that will be resistant to doxorubicin (FIGS. 3-4).

The sample details and workflow for this analysis are illustrated on FIG. 5.

Materials and Methods

Ethical Approval and Clinical Sample Collection

Clinical data and samples for the patients were collected as part of the prospective Cambridge Translational Cancer Research Ovarian Study 04 (CTCROV04) approved by the Institutional Ethics Committee (REC08/H0306/61). Patients provided written, informed consent for participation in this study and for the use of their donated tissue for the laboratory studies carried out in this work.

Sample Processing for Organoids

Samples were obtained from surgical resection, ward drains or surgical washings. Solid tumours were assessed by a pathologist and only tumour samples with 50% cellularity were attempted to grow.

Sample Processing for Spheroids

Ascitic fluid was collected from patients between 100 ml-2 L volume. The fluid was initially gently centrifuged at 800×g for 5 minutes and the majority of the supernatant was removed. The sample was filtered using autoclaved muslin cloth, the flow trough was then filtered again using a cell strainer at 40 µm. Spheroids from the strainer were then recovered by a 10 ml wash with PBS and centrifuged at 1500 rpm for 5 min. The spheroid fraction was divided in two: a cell pellet for DNA extraction; and resuspension of cells in filtered acellular ascitic supernatant and 8% DMSO for the drug screen. Spheroids were thawed and put in media overnight to fully recover before dispensing for the drug screen.

Sample Processing for Tissues

FFPE tissue blocks were cut as 8 µm sections and tumour-enriched regions were recovered by macrodissection based on regions marked on an adjacent haematoxylin-and-eosin-stained section by the study pathologist. DNA was extracted from 3-10 sections using QIAmp DNA Micro kit (Qiagen) with the following modification to the original protocol: an additional incubation step with Buffer ATL at 95° C. for 15 minutes was introduced before adding proteinase K. The paraffin was removed using a xylene/ethanol method.

Sample Processing for ctDNA

Plasma samples were collected from patients with high grade serous ovarian recruited into OV04 prospective clinical study at Addenbrooke's Hospital, Cambridge, UK, approved by the local research ethics committee (REC reference numbers: 07/Q0106/63; and NRES Committee East of England—Cambridge Central 03/018). Written informed consent was obtained from all patients, and blood samples were collected before and after initiation of treatment with surgery or chemotherapeutic agents. We focused on selected plasma timepoints collected before primary chemotherapy treatment and before doxorubicin treatment (usually $2^{nd}$ or $3^{rd}$ line of therapy). For small number of patients were analysed the plasma timepoints collected at the end of doxorubicin treatment.

DNA was extracted from 2 or 4 mL of plasma using the QIAamp circulating nucleic acid kit (Qiagen) or QIAsymphony (Qiagen) according to the manufacturer's instructions. 10 ul of extracted circulating nucleic acids was taken as an input for whole genome library preparation using ThruPLEX DNA-Seq (Takara) library prep kit with the following modifications: no DNA shearing was performed, 14 PCR cycles was applied, library purification using Ampure beads (Beckman Coulter) was performed separately for each sample, elution was performed using 20 ul of Tris EDTA buffer. Generated libraries were quantified using Fragment Analyser NGS kit (Agilent Technologies) diluted to 10 nmol/l and pooled in the same proportions. All libraries were sequenced using NovaSeq S2 (Illumina) using PE-150 bp mode to achieve at least 80 mln read per sample.

Organoid Derivation

Tumour samples were washed in PBS, minced into 2 mm pieces using scalpels and incubated with gentamicin (50 µg/ml), Bovine Serum Albumin Fraction V (1.5%), insulin (5 µg/mL), collagenase A (1 mg/mL) and hyaluronidase (100 U/ml) for 1-2 h at 37° C. Following incubation, the mixture was filtered and the cell suspension was spun down and washed with PBS. Ascites fluid was centrifuged at 450 g for 5 min. Cells were then washed with PBS and centrifuged at 400 g for 5 min. The isolated cells were resuspended in 7.5 mg/ml basement membrane matrix (Cultrex BME RGF type 2 (BME-2), Amsbio) supplemented with complete media and plated as 20 µl droplets in a 6-well plate. After allowing the BME-2 to polymerize, complete media was added and the cells left at 37° C. Complete media: AdDMEM/F12 medium supplemented with HEPES (1×, Invitrogen), Glutamax (1×, Invitrogen), penicillin/streptomycin (1×, Invitrogen), B27 (1×, Invitrogen), N2 (1×, Invitrogen), Wnt3a-conditioned medium (25% v/v), RSPO1-conditioned medium (25% v/v), recombinant Noggin protein (100 ng/ml, Peprotech), epidermal growth factor (EGF, 10 ng/ml, Peprotech), fibroblast growth factor 10 (FGF10, 100 ng/ml, Peprotech), nicotinamide (1 mM, Sigma), SB431542 (0.5 µM, Cambridge Biosciences), and Y27632 (9 µM, Abmole).

Organoid Culture

Organoid culture medium was refreshed every 2 days. To passage the organoids, the domes were scraped and collected in a falcon tube, TrypLE (Invitrogen) was added and they were incubated at 37° C. for approximately 10 min. The suspension was centrifuged at 800 g for 2 min and the cell pellet was resuspended in 7.5 mg/ml BME-2 supplemented with complete media and plated as 20 µl droplets in a 6-well plate. After allowing the BME-2 to polymerize, complete media was added and cells incubated at 37° C. DNA was extracted from cell pellets using the Qiagen Allprep DNA/RNA extraction kit according to manufacturer instructions.

In Vitro Doxorubicin Treatment

An 8-point half-log dilution series of doxorubicin starting at 30 µM was dispensed into 384 well plates using an Echo™ 550 acoustic liquid handler instrument (Labcyte) and kept at −20° C. until used. Organoid plates were spun down and 50 µl of suspension added per well using a Multidrop™ Combi Reagent Dispenser (Thermo-Fisher). Following 5 days of drug incubation cell viability was assayed using 30 µl of CellTiter-Glo™ (Promega). Screens were performed in technical triplicate. An untreated control was used to normalise response values to be equivalent to the percentage of viable cells remaining. To assist with dose response curve fitting, dummy values were added for each sample below and above the minimum and maximum dose ranges at 100% viable cells with a dose of 1e-03 µM and 0% viable cells at a dose of 300 µM. A 4 parameter log-logistic model was used to fit dose response curves, which includes the IC50 parameter used here. Fitting was performed using the drm function in the drc package in R (Ritz et al., 2015). For spheroid samples, the IC50 values were scaled by the inverse of the tumour purity to account for increased cell viability due to normal cell contamination.

DNA Sequencing

Whole-genome sequence libraries were prepared from 75 ng DNA using SMARTer Thruplex DNA-Seq (Takara) protocol. DNA from each sample was sheared on Covaris LE220 (Covaris): duty cycle—30%, intensity—5.0, bursts per sec—50, duration—120 sec, peak incident power—180, temperature 20° C., water level—4. All samples underwent 7 PCR cycles. Library quality and quantity were assessed with D5000 on 4200 Tapestation according to the supplier's recommendations. Libraries were then pooled together and sequenced using PE-50 mode on NovaSeq SP aiming for 10 million reads per sample.

Quality Control and Sample Filtering

All samples in this study underwent a series of quality control (QC) tests, with failed samples being removed from further analysis. A summary of filtering criteria and number of samples retained for further analysis can be found in FIG. 5. The following QC criteria were used:

Repeat samples (organoid, spheroid and tissue): Each of the sample sets presented here contained at least one patient which had multiple samples profiled. In each case, a single sample was chosen for further analysis.

Drug screen (organoid and spheroid samples): Samples showing greater than 20% standard deviation in cell viability across more than 3 dose concentrations were removed from downstream analysis.

Copy number (tissue and ctDNA): Two key factors affect the ability to accurately quantify copy number signature exposures: 1) insufficient tumour genome sequence coverage causing under-segmentation and loss of signal, 2) formalin-mediated DNA degradation causing over-segmentation of the genome and signal contamination. Factor 1 is commonly caused by the tumour purity of a sample being too low. Therefore we removed all tissue samples with a purity less than 40%. To deal with factor 2, we removed all samples (tissue and ctDNA) showing more than 250 segments across their genome.

Absolute Copy-Number Fitting

Reads were aligned against the human genome assembly GRCh37 using BWA-MEM (Li & Durbin, 2009). Duplicates were marked using Picard (Broad Institute, 2018) and relative copy number was computed using QDNAseq (Scheinin et al., 2014) with a bin size of 30 kb. Absolute tumour copy number (the number of chromosome copies of each DNA segment in the tumour cells in a sample) was computed for every bin across each sample. Each segmented relative copy number bin estimate j was transformed from relative copy number (rCN) to absolute copy number (aCN) as follows:

$$aCN_j = \frac{1}{purity} \cdot \left(\frac{rCN_j}{d} - 2 \times (1 - purity)\right)$$

where purity is the fraction of tumour cells in the sample, and d is a constant proportional to the read depth, which is computed from the mean relative copy number of the sample, r, and the average absolute copy number of the tumour cells in the sample, ploidy:

$$d = \frac{r}{(ploidy \times purity + 2 \times (1 - purity))}$$

Both purity and ploidy were unobserved in the data and were estimated using a grid search of purities ranging from [0.05,1] in 0.01 increments and ploidies ranging from [1.8,8] in increments of 0.1, minimising the following mean squared error:

$$e_{purity,ploidy} = \frac{1}{J} \cdot \sum_{j=1}^{J} (aCN - \text{round}(aCN))^2$$

Organoid samples were assumed 100% pure so purity was fixed to 1 and a search was only performed across ploidy states. Purity/ploidy values were excluded from consideration if they resulted in a fit which showed greater than 10 megabases of the genome with homozygous loss. For tissue samples, an additional filter was used, removing fits which did not show at least one genomic segment at every integer copy number state from 1 to ploidy.

Copy Number Signature Computation

Copy number features were calculated from the absolute copy number profiles as detailed in Macintyre et al. (2018). Briefly, absolute copy number profiles were summarised by calculating, for each sample, the genome-wide distribution of six features associated with copy number (CN) events:

Segment size—the length of each genome segment;

Breakpoint count per 10 MB—the number of genome breaks appearing in 10 MB sliding windows across the genome;

Change-point copy-number—the absolute difference in CN between adjacent segments across the genome;

Segment copy-number—the observed absolute copy-number state of each segment;

Breakpoint count per chromosome arm—the number of breaks occurring per chromosome arm;

Length of segments with oscillating copy-number—a traversal of the genome counting the number of contiguous CN segments alternating between two copy-number states, rounded to the nearest integer copy-number state.

For each sample, a sum of posterior probability vector was calculated using the feature component definitions as outlined in Macintyre et al., (2018) (see Table 1 above) and the predict function in the flexmix package in R (Grün et al., 2008).

The sum of posterior probability vectors were used to compute signature exposures using the LCD function in the YAPSA package in Bioconductor (rdrr.io/bioc/YAPSA/f/README.md) and the signature definition matrix reported in Macintyre et al., (2018) (see Tables 1 and 2). The LCD function in this package can calculate exposures for known signatures, given a predefined signature weight matrix.

Classifying Samples as Sensitive or Resistant to Doxorubicin

Organoid and spheroid samples: We determined an IC50 threshold which divided the samples into those considered sensitive or resistant based on the clinical characteristics of the patients. As our in vitro drug screen is analogous to patients being treated with Doxorubicin as a monotherapy following first line treatment with platinum based chemotherapy, we estimated the expected number of sensitive samples based on response observed in clinical trials. Patients resistant to platinum chemotherapy are expected to have an 18% response rate to Doxorubicin monotherapy (Mutch et al., 2007; O'Byrne et al., 2002; Kaye et al., 2012; Ferrandina et al., 2008; Gordon et al., 2004; Pujade-Lauraine, et al., 2012; Rose et al., 2007), and sensitive patients a 28% response rate (Gordon et al., 2001). Patients who had relapsed disease less than 6 months after first-line platinum based chemotherapy were considered resistant and greater than 6 months sensitive (see Table 3). These data allowed us to estimate the expected number of sensitive organoids to be approximately 2 (5×0.28+5×0.18=2.3) and the sensitive spheroids to be 4 (8×0.28+7×0.18=3.5). Samples were ranked based on their IC50 and a threshold set yielding the expected number of sensitive samples in each case.

TABLE 3

Platinum sensitivity status for organoid and spheroid samples

| Patient ID | Sample type | Sample ID | Platinum sensitivity |
|---|---|---|---|
| 75 | organoid | 23868org | sensitive |
| 297 | organoid | 54276org | resistant |
| 366 | organoid | 32077org | sensitive |
| 409 | organoid | 54288org | resistant |
| 413 | organoid | 54327org | sensitive |
| 466 | organoid | 118976org | sensitive |
| 571 | organoid | 151773org | sensitive |
| 627 | organoid | 119127org | resistant |
| 788 | organoid | 119178org | resistant |
| 920 | organoid | 151723org | resistant |
| 333 | spheroid | 118947 | sensitive |
| 338 | spheroid | 54356 | sensitive |
| 364 | spheroid | 32072 | resistant |
| 409 | spheroid | 54289 | resistant |
| 413 | spheroid | 54327 | sensitive |
| 466 | spheroid | 118976 | sensitive |
| 525 | spheroid | 80720 | sensitive |
| 626 | spheroid | 119016 | resistant |
| 648 | spheroid | 80601 | resistant |
| 669 | spheroid | 80630 | sensitive |
| 687 | spheroid | 118902 | resistant |
| 788 | spheroid | 119178 | resistant |
| 800 | spheroid | 119120 | resistant |
| 839 | spheroid | 119025 | sensitive |
| 875 | spheroid | 119136 | sensitive |

Tissue samples: Following treatment with Doxorubicin patients were assessed for response using clinical symptoms, GCIG CA125 criteria or CT imaging and allocated to one of 3 response categories: complete, stable or progressive (see Table 4). These categories are representative of those outlined in the RECIST 1.1 criteria (Rustin et al., 2011).

TABLE 4

Response status and prediction for retrospective tissue samples

| Patient ID | Response | Predicted resistant |
|---|---|---|
| 828 | Complete | FALSE |
| 79 | Stable | FALSE |
| 525 | Stable | FALSE |
| 527 | Stable | FALSE |
| 545 | Stable | FALSE |
| 713 | Stable | FALSE |
| 21 | Progressive | TRUE |
| 25 | Progressive | FALSE |
| 39 | Progressive | FALSE |
| 47 | Progressive | FALSE |
| 63 | Progressive | TRUE |
| 71 | Progressive | TRUE |
| 112 | Progressive | FALSE |
| 116 | Progressive | FALSE |
| 135 | Progressive | TRUE |
| 139 | Progressive | TRUE |
| 202 | Progressive | TRUE |
| 292 | Progressive | FALSE |
| 7 | Progressive | TRUE |
| 49 | Progressive | TRUE |
| 107 | Progressive | TRUE |
| 236 | Progressive | TRUE |
| 282 | Progressive | TRUE |
| 516 | Progressive | TRUE |

Predictive Performance Assessment

For the training (organoid), validation (spheroids) and retrospective (tissue) analyses, performance was assessed using specificity and sensitivity for predicting resistance to doxorubicin. Specificity was considered as the proportion of sensitive samples correctly identified and specificity as the proportion of resistant samples correctly identified. In order to assess the significance of the observed sensitivity a permutation test was performed. All possible resistant/sensitive sample labels were computed, a predictive threshold determined that would yield 100% specificity given the sensitive sample labels, and then sensitivity recorded. The resulting distribution of all observed sensitivity values was used to determine the probability of observing a sensitivity greater than or equal to the observed sensitivity.

Progression Free Survival Analysis

The time to progression for each patient was recorded as the number of days from first administration of Doxorubicin, until date of recorded progression determined by either clinical symptoms, GCIG CA125 criteria or progressive disease on CT imaging. A Cox proportional hazards model was fit with signature 6 exposure >0 as a covariate using the survival package in Bioconductor (Therneau, 2020). Signature 6 exposure <1% was considered to be=0. A Kaplan-Meier curve was generated using the survminer package in Bioconductor (Kassambara et al., 2019).

Example 1: Signature 6 Exposure Predicts Resistance to Doxorubicin in Primary Ovarian Cancer Organoids and in Patient-Derived Spheroids In this example, the inventors set out to test the hypothesis that characteristics of copy number features indicative of the presence of focal amplifications could be indicative of resistance to chemotherapies that induce micronuclei, using ovarian cancer organoids. In particular, 10 primary ovarian cancer organoids were treated with doxorubicin on an 8-point log doubling increasing scale (in triplicate) and an IC50 reduction in cell viability was used as a response measure. Given the clinical characteristics of the patients from which the organoids were derived, the predicted sensitivity rate to doxorubicin across the organoids was around 20%. Therefore, the two organoids with the lowest IC50 were considered sensitive and the 8 remaining organoids as resistant (FIG. 1). Signature 6 exposure was calculated for each organoid and a cut point of exposure >0 selected for predicting resistance at 100% specificity and 100% sensitivity.

Figure 2:
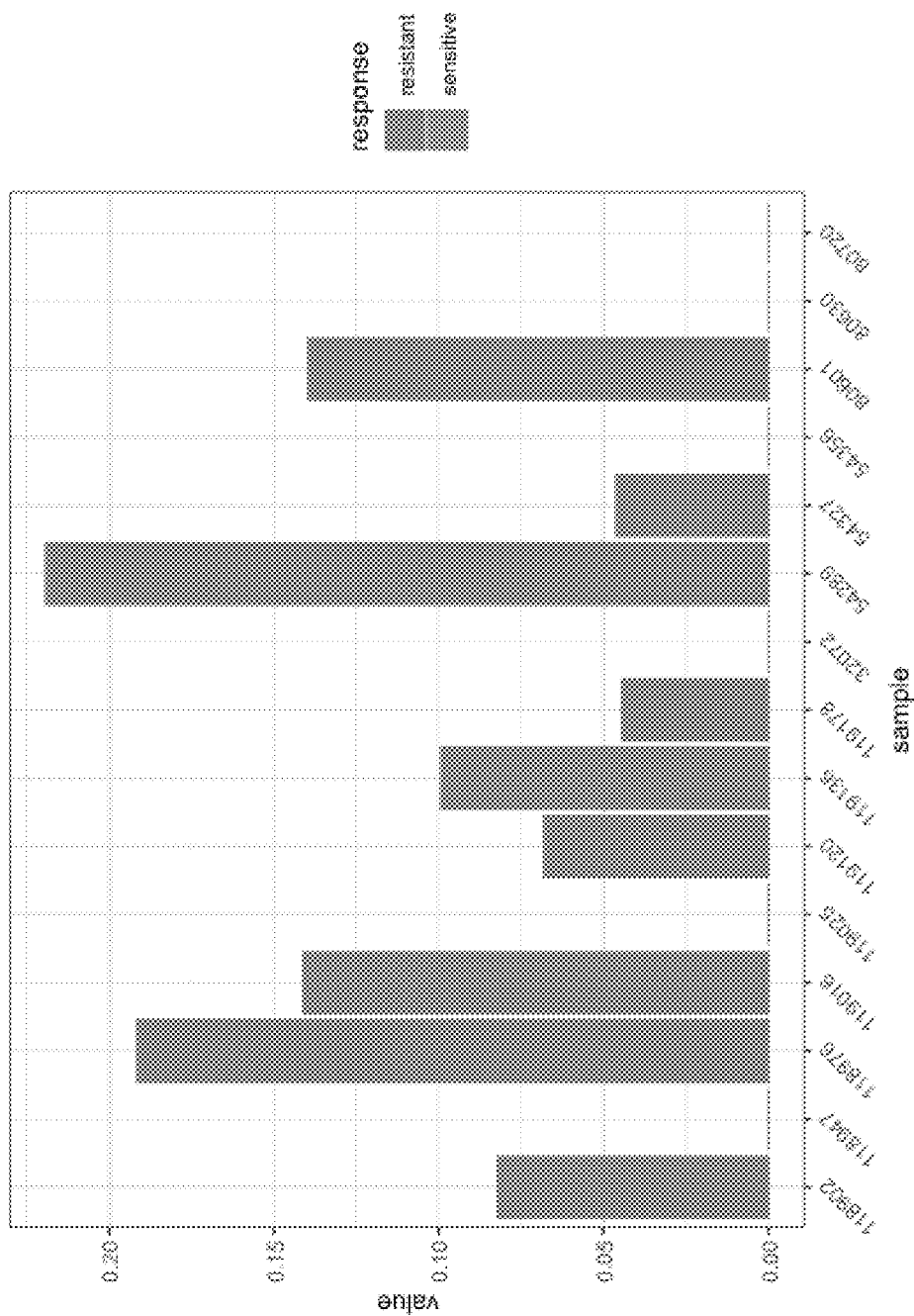
FIG. 2. Doxorubicin response correlates with copy number signature 6 exposure in patient-derived spheroids: copy number signature (signature 6) exposure was calculated (y axis) for 12 patient derived spheroids from ascites fluid. Doxorubicin IC50 (drug concentration which induces a 50% reduction in cell viability) was measured for each of these samples and the 3 samples with the lowest IC50 (first 3 samples on the left, x axis) were deemed sensitive based predicted sensitivity rate to doxorubicin in the patient population from which the spheroids were derived. With a cut-off of exposure >0, 5 samples were predicted to be sensitive to doxorubicin (54356, 80630, 80720, 54327, 119025—where the last two had IC50 higher than the 3 samples deemed sensitive), and 7 samples were predicted to be resistant (119016, 54075, 80601, 54289, 118902, 119178, 119120—all of which had IC50 deemed resistant).

The cut off defined using the organoid data was then evaluated in 12 patient derived spheroids from ascites fluid, treated with doxorubicin in vitro as above. Again the samples with the lower 4 IC50 were classed as sensitive with remaining being classed as resistant. As shown on FIG. 2, those with no exposure to signature 6 were correctly identified as sensitive, resulting in a 100% specificity in this validation data. Two samples were predicted as sensitive which were in fact resistant (118947 & 119025), resulting in 82% sensitivity.

Figure 3:
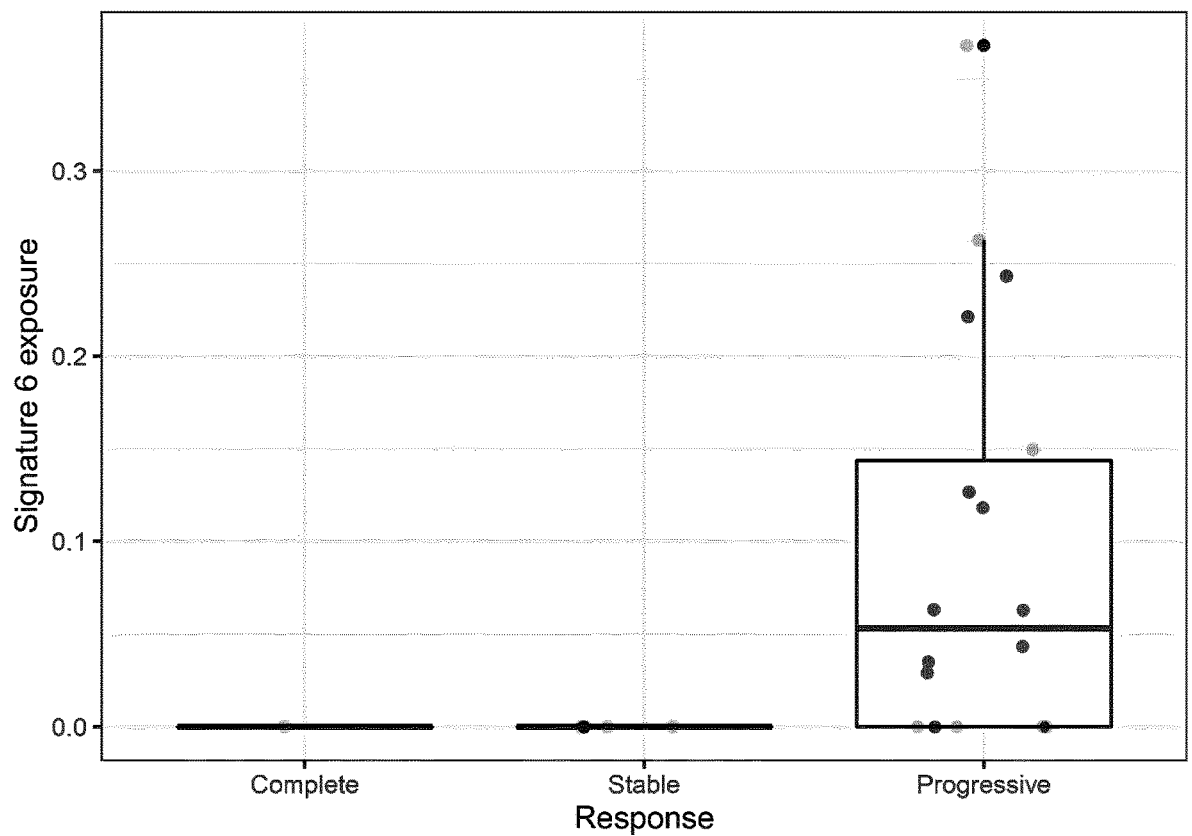
FIG. 3. Copy number signature exposure predicts resistance to doxorubicin in an ovarian cancer patient cohort: Copy number signature 6 exposure (y axis) was calculated for 24 ovarian cancer patients in the CTCR-OV04 cohort, an ovarian clinical trial established to identify biomarkers of response for doxorubicin. Patients were classified in 4 response categories (x axis): complete response, partial response (0/24 patients in this set), stable, and progressive disease. Using a cut-off on copy number signature exposure of >0, progressive and stable cases were identified as resistant to doxorubicin with a sensitivity of 0.5.

Example 2: Signature 6 Exposure Predicts Resistance to Doxorubicin in an Ovarian Cancer Patient Cohort In this example, the inventors set out to validate the test developed in example 1 retrospectively on a patient cohort treated with doxorubicin. CTCR-OV04 is an ovarian clinical study established to identify biomarkers of response. The inventors evaluated signature 6 exposure in this patient population. After QC and filtering there was response data and signatures for 24 patients. Signature 6 exposure levels were evaluated for patients in 4 overall response categories: complete response, partial response (none of the 24 patients in this cohort were in this category), stable and progressive (FIG. 3).

Figure 4:
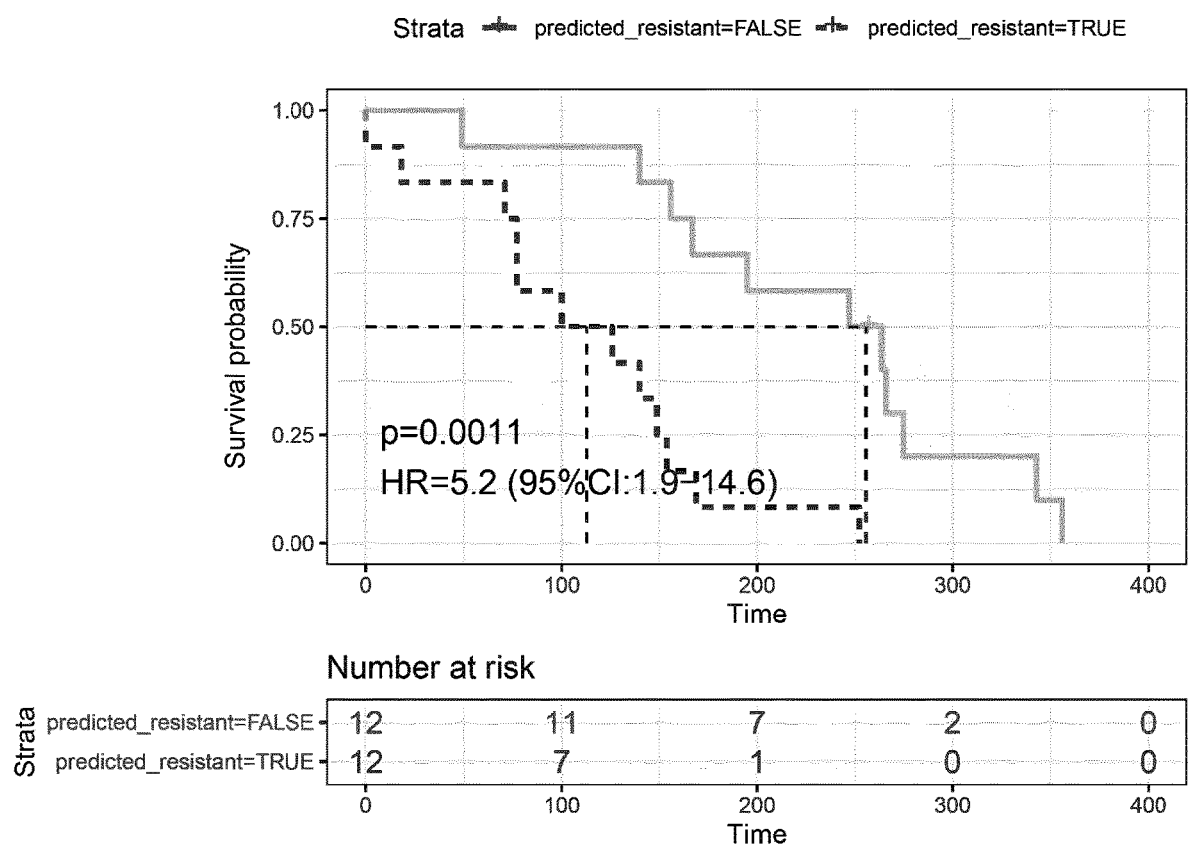
FIG. 4. Copy number signature exposure predicts survival. Kaplan-Meier curves were generated separately for patients predicted as resistant (signature 6 exposure >0) and patients predicted as sensitive. Patients predicted as resistant were approximately 5 times more likely to see their disease progress compared to those predicted as sensitive according to a cox-proportional hazards model fitted with signature 6 exposure >0 as a covariate (HR 5.2, p-value 0.0011, log-rank test).

In this cohort, using a cut-off on signature 6 exposure of 0, the inventors identified progressive cases as resistant to doxorubicin with a sensitivity of 0.5 (i.e. 50% of cases that are in fact resistant are predicted to be sensitive, or in other words 50% of the resistant patients are identified) and a specificity of 1 (i.e. all cases that are predicted as resistant are in fact resistant, in other word no case is predicted as resistant when it is in fact sensitive) (p-value=0.05). Patients predicted as resistant were approximately 5 times more likely to see their disease progress compared to those predicted as sensitive according to a cox-proportional proportional hazards model (FIG. 4, HR 5.2, p-value 0.0011, log-rank test).

With any such test, there is a trade-off between the number of false positives and the number of false negatives identified, depending on the cut-off point used. As the current state of care for ovarian cancer is that most patients do receive doxorubicin at some point during the course of their treatment, the confident accurate identification of patients that are resistant (true negatives, TNs) is more important than the identification of patients that are sensitive (true positives, TPs). Indeed, failing to provide doxorubicin treatment to a patient that may have responded to it is less desirable than providing doxorubicin treatment to some patients that will not respond to it. In other words, any patient that can be spared an unnecessary treatment is an improvement over the current status quo. Therefore, the inventors chose to apply a cut-off that enabled them to identify resistant patients with 100% accuracy, despite the reduced sensitivity of the test (larger number of false positives).

Figure 6A:
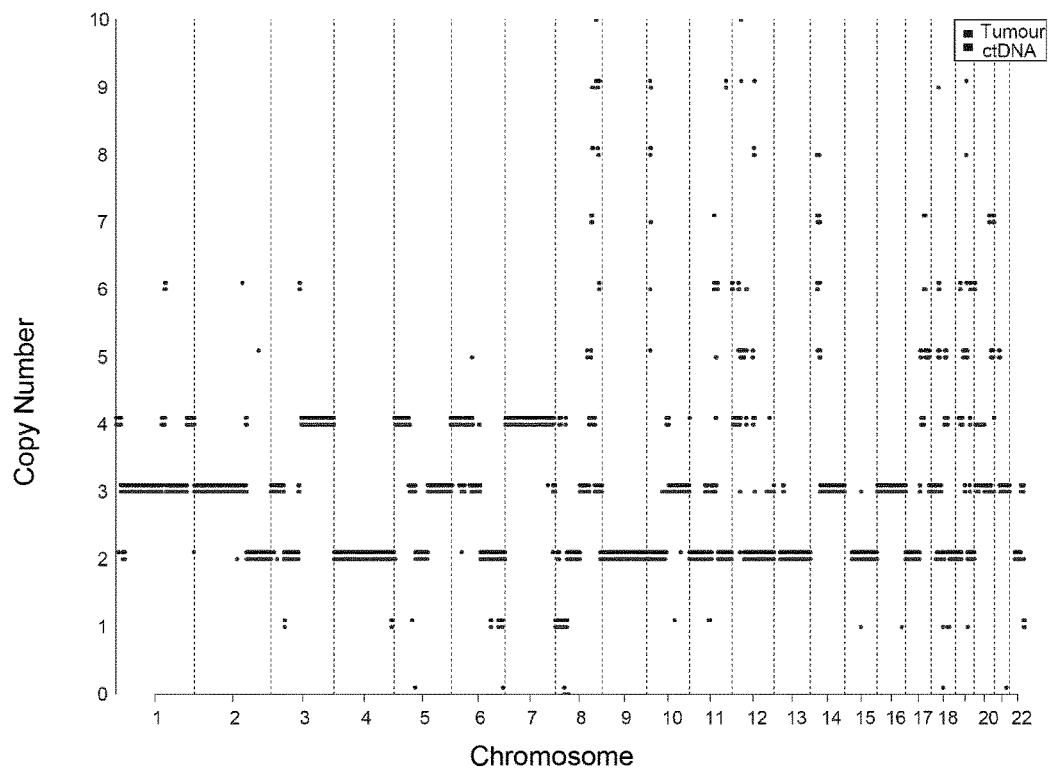
FIG. 6. Copy number signature exposure can be obtained from tumour tissue samples or from ctDNA samples. (A) Matched tumour tissue sample and blood sample ctDNA copy number profiles for Patient 139, showing high level of agreement. (B) Exposure of signatures 1-7 calculated from the matched tumour tissue sample (left) and ctDNA sample (right) for Patient 139, showing high level of agreement and in particular exposure to signature 6>0 in both cases (resulting the patient being classified as resistant using either type of samples).
Figure 6B:
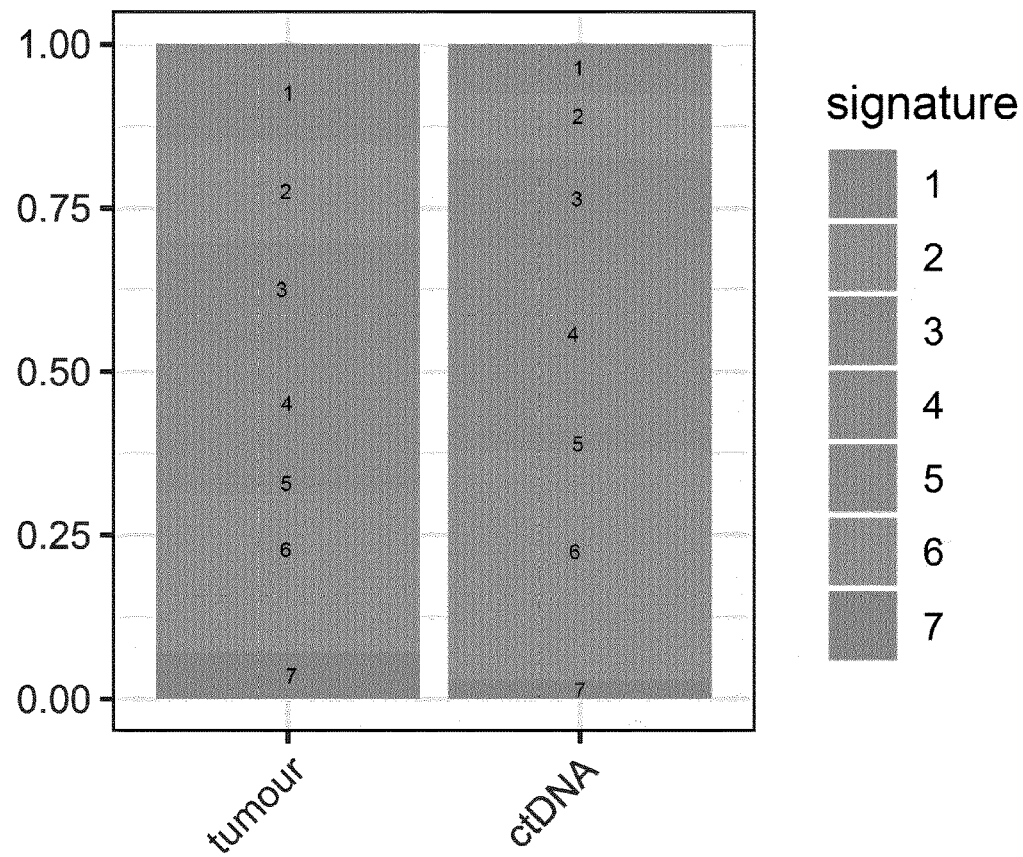

The inventors further set out to verify that samples comprising circulating tumour DNA could be used in the methods described herein in a similar way as samples comprising tumour DNA extracted directly from tumour tissue. Thus, copy number profiles were obtained from cell free DNA extracted from plasma samples and from DNA extracted from matched tumour tissue, for patients where sequencing data was available for both types of samples. An example of such a copy number analysis for matched samples is shown on FIG. 6 (patient 139), where FIG. 6A shows the copy number profile for the tumour tissue and for the matched ctDNA sample, and FIG. 6B shows the corresponding calculated signature exposures. The data shows that very similar copy number profiles could be obtained from the ctDNA sample and the tumour tissue sample, and that similar signature exposures were therefore obtained. This indicates that copy number features indicative of focal amplifications (such as exposure to signature 6) can be calculated from ctDNA samples as well as tumour tissue samples. In particular, the exposure to signature 6 was found to be similar between the two types of samples, and both accurately classified the patient as resistant (See Table 4). Thus, both types of samples can be used to predict resistance to doxorubicin.

Example 3: Copy Number Features Indicative of Focal Amplifications Show Differences Between Patients that are Resistant vs Sensitive to Doxorubicin The data from 18 patients from Example 2 (selected solely due to availability of the data at the time) was used to determine whether copy number features associated with components that are highly weighted in copy number signature 6 could have utility as predictors of resistance to doxorubicin. The behaviour of the segment copy number feature, the copy number change-point feature and the segment size feature was investigated for the sensitive and resistant samples.

In particular, for the segment copy number feature, the following values were calculated for each sample: the average segment copy number, the median segment copy number, the number of copy number events with a segment copy number above 5, the proportion of copy number events that have a segment copy number above 5, the sum-of-posterior probabilities for segment copy number component 8 (cn8, N(30.8672269, 23.15811)—see Table 1), and the sum-of-posterior probabilities for segment copy number component 7 (cn7, N(8.39260927, 3.50149434)—see Table 1). The results of this are shown in Table 5, where the symbol in brackets next to the patient ID indicates the response status (S=stable, C=complete, P=progressive) and rows shaded in grey are those patients predicted to be resistant on the basis of signature 6 exposure (Example 2), avg seg cn=average segment copy number, median seg cn=median segment copy number, # events cn>5=number of copy number events with a segment copy number above 5, % events cn>5=proportion of copy number events that have a segment copy number above 5, sum-of-pos cn8=sum-of-posterior probabilities for segment copy number component 8, sum-of-pos cn7=the sum-of-posterior probabilities for segment copy number component 7.

For the copy number change-point feature, the following values were calculated for each sample: the average copy number change-point, the median copy number change-point, the number of copy number events with a copy number change-point above 4, the proportion of copy number events that have a copy number change-point above 4, the sum-of-posterior probabilities for copy number change-point component 7 (cp7, N(28.7346654, 22.0551593)—see Table 1), the sum-of-posterior probabilities for copy number change-point component 6 (cp6, N(7.3149416, 3.45921997)—see Table 1), the sum-of-posterior probabilities for copy number change-point component 5 (cp5, nN(3.00685766, 1.03958107)—see Table 1). The results of this are shown in Table 6, where the symbol in brackets next to the patient ID indicates the response status (S=stable, C=complete, P=progressive) and rows shaded in grey are those patients predicted to be resistant on the basis of signature 6 exposure (Example 2), avg cp=average copy number change-point, median cp=median copy number change-point, # events cp>4=number of copy number events with a copy number change-point above 4, % events cp >4=proportion of copy number events that have a copy number change-point above 4, sum-of-pos cp7=sum-of-posterior probabilities for copy number change-point component 7, sum-of-pos cp6=sum-of-posterior probabilities for copy number change-point component 6, sum-of-pos cp5=sum-of-posterior probabilities for copy number change-point component 5.

For the segment size feature, the following values were calculated for each sample: the number of copy number events with a segment size above 12,000,000 bp, the proportion of copy number events that have a segment size above 12,000,000 bp, the number of copy number events with a segment size below 4,000,000 bp, the proportion of copy number events that have a segment size below 4,000, 000 bp, the sum-of-posterior probabilities for segment size component 7 (ss7, N(16419124.1, 5226151.49)—see Table 1), the sum-of-posterior probabilities for segment size component 8 (ss8, N(29508322.4, 9703791.44)—see Table 1), the sum-of-posterior probabilities for segment size component 9 (ss9, N(58638899, 20499001.4)—see Table 1), the sum-of-posterior probabilities for segment size component 1 (ss1, N(426861.918, 186924.872)—see Table 1), the sum-of-posterior probabilities for segment size component 2 (ss2, N(1081858.4, 407302.128)—see Table 1), and the sum-of-posterior probabilities for segment size component 3 (ss3, N(2233029.82, 749092.036)—see Table 1). The results of this are shown in Table 7, where the symbol in brackets next to the patient ID indicates the response status (S=stable, C=complete, P=progressive) and rows shaded in grey are those patients predicted to be resistant on the basis of signature 6 exposure (Example 2), # events ss>12 Mb=number of copy number events with a segment size above 12,000,000 bp, % events ss>12 Mb=proportion of copy number events that have a segment size above 12,000,000 bp, # events ss<4 Mb=number of copy number events with a segment size below 4,000,000 bp, % events ss<4 Mb=proportion of copy number events that have a segment size below 4,000,000 bp, sum-of-pos ss7=sum-of-posterior probabilities for segment size component 7, sum-of-pos ss8=sum-of-posterior probabilities for segment size component 8, sum-of-pos ss9=sum-of-posterior probabilities for segment size component 9, sum-of-pos ss1=sum-of-posterior probabilities for segment size component 1, sum-of-pos ss2=sum-of-posterior probabilities for segment size component 2, and sum-of-pos ss3=sum-of-posterior probabilities for segment size component 3.

this, a threshold of between 36 and 60 (or between 36 and 50, between 38 and 48, between 40 and 45, such as e.g. 42) events with a segment copy number above 5 could be used, resulting in 6/6 of the sensitive patients being identified as sensitive and 3/12 of the resistant patients being identified as resistant.

Instead or in addition to this, a threshold of about 5% (or between 25 and 28%) of events with a segment copy number above 5 could be used, resulting in 5/6 of the sensitive patients (and 6/6, respectively) being identified as sensitive and 7/12 of the resistant patients (or 4/12, respectively) being identified as resistant. Instead or in addition to this, a threshold of between 7e-5 and 1.1e-4 for the sum-of-posterior probabilities of copy number component 8 could be used, resulting in 5/6 of the sensitive patients being identified as sensitive and 5/12 of the resistant patients being identified as resistant. Instead or in addition to this, a threshold of about 1.5e-3 for the sum-of-posterior probabilities of copy number component 8 could be used, resulting in 6/6 of the sensitive patients being identified as sensitive and 4/12 of the resistant patients being identified as resistant. Instead or in addition to this, a threshold of between 2e-3 and 6e-3 for the sum-of-posterior probabilities of copy number component 8 could be used, resulting in 6/6 of the sensitive patients being identified as sensitive and 3/12 of the resistant

TABLE 5

Characteristics of the segment copy number feature in tissue sample data

| Patient ID | avg seg cn | median seg cn | max seg cn | # events cn >5 | % events cn >5 | sum-of-pos cn8 | sum-of-pos cn7 |
|---|---|---|---|---|---|---|---|
| 828 (C) | 2.147302 | 2.023929 | 6.844130 | 3 | 4.000000 | 4.930479e-05 | 0.0012554609 |
| 79 (S) | 2.010924 | 1.965767 | 5.095439 | 1 | 1.098901 | 4.982559e-05 | 0.0008817503 |
| 525 (S) | 2.224946 | 2.068175 | 4.426016 | 0 | 0.000000 | 3.802617e-05 | 0.0008200235 |
| 527 (S) | 2.269401 | 2.042489 | 6.812188 | 5 | 2.336449 | 6.129645e-05 | 0.0016759922 |
| 545 (S) | 2.630762 | 2.807298 | 6.723950 | 1 | 3.030303 | 1.609349e-05 | 0.0007322496 |
| 713 (S) | 4.003818 | 3.824326 | 19.520784 | 35 | 23.333333 | 1.100231e-03 | 0.0111078931 |
| 21 (P) | 2.368788 | 2.061603 | 6.690685 | 4 | 2.352941 | 4.043984e-05 | 0.0013428192 |
| 25 (P) | 2.265608 | 2.082485 | 5.648913 | 3 | 2.238806 | 4.722299e-05 | 0.0011216334 |
| 39 (P) | 2.165315 | 2.080123 | 3.929286 | 0 | 0.000000 | 3.224945e-05 | 0.0007452478 |
| 47 (P) | 2.447792 | 2.197755 | 10.173171 | 11 | 6.010929 | 1.116134e-04 | 0.0032906265 |
| 63 (P) | 5.077528 | 4.087224 | 100.411854 | 61 | 37.195122 | 2.519267e-03 | 0.0173353421 |
| 71 (P) | 3.645150 | 3.391058 | 10.045092 | 29 | 15.183246 | 8.102011e-05 | 0.0048701025 |
| 112 (P) | 2.482090 | 2.064806 | 6.116134 | 6 | 4.511278 | 6.209603e-05 | 0.0017164591 |
| 116 (P) | 2.593973 | 2.065268 | 9.269678 | 6 | 5.405405 | 6.445220e-05 | 0.0030375041 |
| 135 (P) | 5.500976 | 4.689479 | 34.306951 | 102 | 41.975309 | 6.141047e-03 | 0.0262317575 |
| 139 (P) | 5.101391 | 3.157907 | 50.656935 | 64 | 28.070175 | 7.922941e-03 | 0.0223279104 |
| 202 (P) | 4.261174 | 3.912181 | 21.550659 | 31 | 28.703704 | 1.552006e-03 | 0.0113230421 |
| 292 (P) | 1.955397 | 2.032471 | 5.997945 | 2 | 1.538462 | 6.883981e-05 | 0.0011674871 |

The data in Table 5 indicates that a threshold for the average segment copy number of between 2.65 and 3.60 (or between 2.8 and 3.4, between 3 and 3.2, or about 3.15, such as e.g. 3.146530) could be used to separate samples from resistant vs sensitive patients, resulting in 5/6 of the sensitive patients being identified as sensitive and 5/12 of the resistant patients being identified as resistant. Instead or in addition to this, a threshold of between 2.85 and 3.1 (or between 2.9 and 3.05, between 2.95 and 3.05, or about 3, such as e.g. 3.000824) for the median segment copy number could be used, resulting in 5/6 of the sensitive patients being identified as sensitive and 5/12 of the resistant patients being identified as resistant. Instead or in addition to this, a threshold of between 7 and 9 (or between 7.5 and 8.5, between 8 and 9, or about 8.5) for the maximum segment copy number could be used, resulting in 5/6 of the sensitive patients being identified as sensitive and 7/12 of the resistant patients being identified as resistant. Instead or in addition to patients being identified as resistant. Instead or in addition to this, a threshold of 0.0017 for the sum-of-posterior probabilities of copy number component 7 could be used, resulting in 5/6 of the sensitive patients being identified as sensitive and 8/12 of the resistant patients being identified as resistant. Instead or in addition to this, a threshold of between 0.012 and 0.017 for the sum-of-posterior probabilities of copy number component 7 could be used, resulting in 6/6 of the sensitive patients being identified as sensitive and 3/12 of the resistant patients being identified as resistant. Instead or in addition to this, a threshold of between 2e-3 and 1.5e-2 (such as e.g. 0.006882869) for the sum-of-posterior probabilities of any of (i.e. one or both) copy number components 7 and 8 could be used, resulting in 5/6 of the sensitive patients (or 6/6, above 1.11e-2) being identified as sensitive and 6/12 of the resistant patients (or 5/12 above 3e-3, 4/12 above 5e-3) being identified as resistant.

TABLE 6

Characteristics of the copy number change-point feature in tissue sample data

| Patient ID | avg cp | median cp | max cp | # events cp >4 | % events cp >4 | sum-of-pos cp7 | sum-of-pos cp6 | sum-of-pos cp5 |
|---|---|---|---|---|---|---|---|---|
| 828 (C) | 0.9944723 | 0.9415299 | 4.007163 | 1 | 1.8867925 | 1.323601e−05 | 2.771318e−04 | 0.004163245 |
| 79 (S) | 1.0573172 | 0.9769108 | 2.267934 | 0 | 0.0000000 | 1.058179e−05 | 1.326782e−04 | 0.002827060 |
| 525 (S) | 1.1584585 | 1.0361165 | 2.225617 | 0 | 0.0000000 | 1.023245e−05 | 1.366641e−04 | 0.003134670 |
| 527 (S) | 0.8707222 | 0.7784600 | 3.176237 | 0 | 0.0000000 | 1.907098e−05 | 2.293483e−04 | 0.004328551 |
| 545 (S) | 1.6660965 | 1.5600377 | 3.876448 | 0 | 0.0000000 | 1.018767e−05 | 2.622988e−04 | 0.005226742 |
| 713 (S) | 2.4019398 | 2.0563907 | 17.562393 | 11 | 8.5937500 | 1.033945e−03 | 4.716663e−03 | 0.044349710 |
| 21 (P) | 1.3284668 | 1.0682097 | 5.709680 | 1 | 0.6756757 | 3.974345e−05 | 1.130750e−03 | 0.012183156 |
| 25 (P) | 1.0130869 | 0.9515234 | 3.626172 | 0 | 0.0000000 | 1.156120e−05 | 1.645553e−04 | 0.003073866 |
| 39 (P) | 0.9935403 | 0.9115496 | 2.365310 | 0 | 0.0000000 | 7.785034e−06 | 9.416096e−05 | 0.001817346 |
| 47 (P) | 1.1400930 | 0.9344969 | 5.034860 | 2 | 1.2422360 | 3.732687e−05 | 8.726254e−04 | 0.012240196 |
| 63 (P) | 3.3044785 | 1.3544487 | 88.760668 | 24 | 16.9014085 | 3.561290e−03 | 7.142379e−03 | 0.033832841 |
| 71 (P) | 1.3285737 | 1.0917875 | 9.015849 | 2 | 1.1834320 | 7.794048e−05 | 2.449876e−03 | 0.012202502 |
| 112 (P) | 1.2060012 | 1.0136620 | 5.216264 | 1 | 0.9009009 | 2.920685e−05 | 7.306476e−04 | 0.007815138 |
| 116 (P) | 1.2087188 | 0.9049111 | 4.276671 | 1 | 1.1235955 | 2.999759e−05 | 6.846563e−04 | 0.013901501 |
| 135 (P) | 2.3718034 | 1.8631313 | 30.429135 | 19 | 8.5972851 | 1.231322e−03 | 1.064421e−02 | 0.043086844 |
| 139 (P) | 3.7884988 | 1.4285675 | 39.520040 | 41 | 19.9029126 | 1.000494e−02 | 2.010276e−02 | 0.029816316 |
| 202 (P) | 2.1285750 | 1.3564708 | 18.008689 | 9 | 10.4651163 | 1.434303e−03 | 6.639154e−03 | 0.024178709 |
| 292 (P) | 1.1726072 | 1.0444167 | 4.029753 | 1 | 0.9259259 | 1.966385e−05 | 3.567927e−04 | 0.008525203 |

The data in Table 6 indicates that a threshold for the average copy number change-point of between 1.2 and 1.328 (or between 1.2 and 1.328, between 1.3 and 1.328, or about 1.328, such as e.g. 1.323483) could be used to separate samples from resistant vs sensitive patients, resulting in 3/6 of the sensitive patients being identified as sensitive and 6/12 of the resistant patients being identified as resistant. Instead or in addition to this, a threshold of between 1.2 and 2.1 for the median copy number change-point could be used, resulting in 3/6 of the sensitive patients (4/6 above 1.7) being identified as sensitive and 5/12 of the resistant patients (4/12 above 1.33) being identified as resistant. Instead or in addition to this, a threshold of between 1.04 and 1.06 (such as e.g. 1.051904) for the median copy number change-point could be used, resulting in 4/6 of the sensitive patients being identified as sensitive and 6/12 of the resistant patients being identified as resistant.

Instead or in addition to this, a threshold of between 4.01 and 5 (or between 4.01 and 4.025) for the maximum copy number change-point could be used, resulting in 5/6 of the sensitive patients being identified as sensitive and 10/12 of the resistant patients (or 9/12 above 4.03, 8/12 above 4.28) being identified as resistant. Instead or in addition to this, a threshold of about 18 (e.g. between 17.6 and 18 for the maximum copy number change-point could be used, resulting in 6/6 of the sensitive patients being identified as sensitive and 4/12 of the resistant patients being identified as resistant. Instead or in addition to this, a threshold of about between 18 and 30 for the maximum copy number change-point could be used, resulting in 6/6 of the sensitive patients being identified as sensitive and 3/12 of the resistant patients being identified as resistant.

Instead or in addition to this, a threshold of between 2 and 18 (or between 2 and 8, between 2 and 6, such as e.g. 3) events with a copy number change-point above 4 could be used, resulting in 5/6 of the sensitive patients (6/6 above 11) being identified as sensitive and 6/12 of the resistant patients (4/12 above 2, 3/12 above 9) being identified as resistant. Instead or in addition to this, a threshold of between 2% and 10% (or between 2 and 8%, such as e.g. 5% or between 8.6 and 10%, such as e.g. 8.6%) events with a copy number change-point above 4 could be used, resulting in 5/6 of the sensitive patients (6/6 above 8.6%) being identified as sensitive and 4/12 of the resistant patients (3/12 above 8.6%) being identified as resistant. Instead or in addition to this, a threshold of between 1.91e-5 and 1.1e-3 for the sum-of-posterior probabilities of copy number change-point component 7 could be used (or between 1.035e-3 and 1.23e-3), resulting in 5/6 of the sensitive patients (6/6 above 1.034e-3) being identified as sensitive and 10/12 of the resistant patients (9/12 above 1.97e-5, 7/12 above 3e-5, 4/12 above 4e-5, 4/12 between 1.035e-3 and 1.23e-3) being identified as resistant. Instead or in addition to this, a threshold of between 2.8e-4 and 6.6e-3 for the sum-of-posterior probabilities of copy number change-point component 6 could be used (or between 4.72e-3 and 6.6e-3), resulting in 5/6 of the sensitive patients (6/6 above 4.72e-3) being identified as sensitive and 11/12 of the resistant patients (10/12 above 3.6e-4, 9/12 above 6.9e-4, 8/12 above 7.3e-4, 7/12 above 8.7e-4, 5/12 above 1.2e-3, 4/12 between 4.72e-3 and 6.6e-3) being identified as resistant. Instead or in addition to this, a threshold of between 0.006 and 0.023 for the sum-of-posterior probabilities of copy number change-point component 5 could be used, resulting in 5/6 of the sensitive patients being identified as sensitive and 10/12 of the resistant patients (8/12 above 0.009, 5/12 above 0.013) being identified as resistant. Instead or in addition to this, a threshold of 0.02041483 for the sum-of-posterior probabilities for any of the change-point components in Table 6 could be used, resulting in 5/6 of the sensitive patients being identified as sensitive and 4/12 of the resistant patients being identified as resistant.

TABLE 7

Characteristics of the segment size feature in tissue sample data

| Patient ID | # events ss >12 Mb | % events ss >12 Mb | # events ss <4 Mb | % events ss <4 Mb | # >12 Mb + # <4 Mb | sum-of-pos ss1 |
|---|---|---|---|---|---|---|
| 828 (C) | 47 | 62.66667 | 14 | 18.66667 | 61 | 0.005640154 |
| 79 (S) | 51 | 56.04396 | 30 | 32.96703 | 81 | 0.013486211 |
| 525 (S) | 49 | 44.14414 | 53 | 47.74775 | 102 | 0.031024672 |
| 527 (S) | 73 | 34.11215 | 100 | 46.72897 | 173 | 0.018000829 |
| 545 (S) | 27 | 81.81818 | 4 | 12.12121 | 31 | 0.004048530 |
| 713 (S) | 49 | 32.66667 | 78 | 52.00000 | 127 | 0.030477520 |
| 21 (P) | 74 | 43.52941 | 64 | 37.64706 | 138 | 0.028726589 |
| 25 (P) | 61 | 45.52239 | 48 | 35.82090 | 109 | 0.018765127 |
| 39 (P) | 51 | 69.86301 | 12 | 16.43836 | 63 | 0.007266266 |
| 47 (P) | 63 | 34.42623 | 93 | 50.81967 | 156 | 0.034782410 |
| 63 (P) | 52 | 31.70732 | 81 | 49.39024 | 133 | 0.028569541 |
| 71 (P) | 63 | 32.98429 | 83 | 43.45550 | 146 | 0.019268153 |
| 112 (P) | 52 | 39.09774 | 58 | 43.60902 | 110 | 0.025007691 |
| 116 (P) | 47 | 42.34234 | 50 | 45.04505 | 97 | 0.018016982 |
| 135 (P) | 61 | 25.10288 | 138 | 56.79012 | 199 | 0.041823357 |
| 139 (P) | 48 | 21.05263 | 135 | 59.21053 | 183 | 0.035474670 |
| 202 (P) | 34 | 31.48148 | 56 | 51.85185 | 90 | 0.021004902 |
| 292 (P) | 64 | 49.23077 | 38 | 29.23077 | 102 | 0.013488822 |

| Patient ID | sum-of-pos ss2 | sum-of-pos ss3 | sum-of-pos ss7 | sum-of-pos ss8 | sum-of-pos ss9 |
|---|---|---|---|---|---|
| 828 (C) | 0.005198132 | 0.010960890 | 0.013754410 | 0.027823531 | 0.028913912 |
| 79 (S) | 0.019338033 | 0.014250124 | 0.013571903 | 0.030494723 | 0.029512448 |
| 525 (S) | 0.032345801 | 0.011283168 | 0.012053413 | 0.027868334 | 0.023754090 |
| 527 (S) | 0.031754429 | 0.035199473 | 0.022996570 | 0.028860657 | 0.014617331 |
| 545 (S) | 0.002035183 | 0.002552591 | 0.004236167 | 0.008330425 | 0.023814473 |
| 713 (S) | 0.031958892 | 0.026357854 | 0.013576545 | 0.019857529 | 0.017417731 |
| 21 (P) | 0.019551257 | 0.015344410 | 0.023273346 | 0.034903612 | 0.019313757 |
| 25 (P) | 0.020803972 | 0.020338999 | 0.018482288 | 0.036083540 | 0.017797367 |
| 39 (P) | 0.006985681 | 0.005389303 | 0.015719359 | 0.033636211 | 0.028427051 |
| 47 (P) | 0.039914969 | 0.019864814 | 0.019643079 | 0.028132100 | 0.016555315 |
| 63 (P) | 0.030507105 | 0.023997654 | 0.016090303 | 0.022298623 | 0.016175362 |
| 71 (P) | 0.021058723 | 0.032692433 | 0.020948535 | 0.025241949 | 0.016407077 |
| 112 (P) | 0.023249875 | 0.018521508 | 0.017315710 | 0.023277378 | 0.016187200 |
| 116 (P) | 0.023209733 | 0.025902678 | 0.012971966 | 0.023837131 | 0.020988082 |
| 135 (P) | 0.039131805 | 0.030394722 | 0.016855212 | 0.022324287 | 0.011286621 |
| 139 (P) | 0.040349949 | 0.034435082 | 0.014660419 | 0.014187481 | 0.009714799 |
| 202 (P) | 0.032992124 | 0.023128868 | 0.005423815 | 0.014443723 | 0.016793852 |
| 292 (P) | 0.018461421 | 0.014490247 | 0.027381359 | 0.029781304 | 0.022489383 |

The data in Table 7 indicates that a threshold of 130 for the sum of the number of events with a segment size above 12 Mbp and the number of events with a segment size below 4 Mbp could be used to separate samples from resistant vs sensitive patients, resulting in 5/6 of the sensitive patients being identified as sensitive and 6/12 of the resistant patients being identified as resistant. Instead or in addition to this, a threshold of 52 for the number of events with a segment size above 12 Mbp could be used, resulting in 5/6 of the sensitive patients being identified as sensitive and 8/12 of the resistant patients being identified as resistant. Instead or in addition to this, a threshold of 55 for the number of events with a segment size below 4 Mb could be used, resulting in 3/6 of the sensitive patients being identified as sensitive and 8/12 of the resistant patients being identified as resistant. Instead or in addition to this, a threshold of 52 for the number of events with a segment size above 12 Mbp could be used in combination with a threshold of 55 for the number of events with a segment size below 4 Mb, resulting in 5/6 of the sensitive patients being identified as sensitive and 6/12 of the resistant patients being identified as resistant. Instead or in addition to this, a threshold of about 0.02 for the sum-of-posterior probabilities of segment size component 1 could be used, resulting in 4/6 of the sensitive patients being identified as sensitive and 7/12 of the resistant patients being identified as resistant. Instead or in addition to this, a threshold of about 0.032 for the sum-of-posterior probabilities of segment size component 1 could be used, resulting in 6/6 of the sensitive patients being identified as sensitive and 3/12 of the resistant patients being identified as resistant. Instead or in addition to this, a threshold of about 0.032 for the sum-of-posterior probabilities of segment size component 2 could be used, resulting in 5/6 of the sensitive patients being identified as sensitive and 4/12 of the resistant patients being identified as resistant. Instead or in addition to this, a threshold of about 0.033 for the sum-of-posterior probabilities of segment size component 2 could be used, resulting in 6/6 of the sensitive patients being identified as sensitive and 3/12 of the resistant patients being identified as resistant. Instead or in addition to this, a threshold of about 0.03 for the sum-of-posterior probabilities of segment size component 3 could be used, resulting in 5/6 of the sensitive patients being identified as sensitive and 4/12 of the resistant patients being identified as resistant. Instead or in addition to this, a threshold of about 0.033 for the sum-of-posterior probabilities of segment size component 3 could be used, resulting in 6/6 of the sensitive patients being identified as sensitive and 3/12 of the resistant patients being identified as resistant.

Instead or in addition to this, a threshold of about 0.032 for the sum-of-posterior probabilities of any of segment size components 1-3 (i.e. a threshold that applies to one, two or all three) could be used, resulting in 5/6 of the sensitive patients being identified as sensitive and 4/12 of the resistant patients being identified as resistant. Instead or in addition to this, a threshold of about 0.033 for the sum-of-posterior probabilities of any of segment size components 1-3 could be used (i.e. a threshold that applies to one, two or all three), resulting in 6/6 of the sensitive patients being identified as sensitive and 3/12 of the resistant patients being identified as resistant. Instead or in addition to this, a threshold of about 0.014 for the sum-of-posterior probabilities of segment size component 7 could be used, resulting in 5/6 of the sensitive patients being identified as sensitive and 10/12 of the resistant patients being identified as resistant. Instead or in addition to this, a threshold of about 0.023 for the sum-of-posterior probabilities of segment size component 7 could be used, resulting in 6/6 of the sensitive patients being identified as sensitive and 2/12 of the resistant patients being identified as resistant. Instead or in addition to this, a threshold of about 0.029 for the sum-of-posterior probabilities of segment size component 8 could be used, resulting in 5/6 of the sensitive patients being identified as sensitive and 4/12 of the resistant patients being identified as resistant. Instead or in addition to this, a threshold of about 0.031 for the sum-of-posterior probabilities of segment size component 8 could be used, resulting in 6/6 of the sensitive patients being identified as sensitive and 3/12 of the resistant patients being identified as resistant.

Instead or in addition to this, a threshold of about 0.029 for the sum-of-posterior probabilities of any of segment size components 7-9 (i.e. a threshold that applies to one, two or all three) could be used, resulting in 5/6 of the sensitive patients being identified as sensitive and 4/12 of the resistant patients being identified as resistant. Instead or in addition to this, a threshold of about 0.033 for the sum-of-posterior probabilities of any of segment size components 7-9 could be used (i.e. a threshold that applies to one, two or all three), resulting in 6/6 of the sensitive patients being identified as sensitive and 4/12 of the resistant patients being identified as resistant. Instead or in addition to this, a threshold of about 0.02 for the sum-of-posterior probabilities of any of segment size components 7-9 (i.e. a threshold that applies to one, two or all three) could be used in combination with a threshold of about 0.03 for the sum-of-posterior probabilities of any of segment size components 1-3 (i.e. a threshold that applies to one, two or all three), resulting in 4/6 of the sensitive patients being identified as sensitive and 4/12 of the resistant patients being identified as resistant. Instead or in addition to this, a threshold of 0.02041483 for the sum-of-posterior probabilities for any of the segment size components 1-3 and 7-9 in combination (i.e. where the threshold applies to at least one in every group) in Table 7 could be used, resulting in 4/6 of the sensitive patients being identified as sensitive and 8/12 of the resistant patients being identified as resistant. Instead or in addition to this, a threshold of 0.1527743 for the sum-of-posterior probabilities for any of the segment size components in Table 7 could be used (preferably at least one of ss1-3 and at least one of ss7-9 are above this threshold).

In addition to the specific values and ranges of values mentioned above, any threshold that applies to any of the values in Tables 5, 6 or 7, and that, alone or in combination with another threshold that applies to any of the values in Tables 5, 6 or 7 results in 6/6 of the sensitive patients being identified as sensitive, and at least one of the resistant patients being identified as resistant, is explicitly envisaged. Indeed, any such threshold or combination of threshold advantageously results in at least one patient being spared a treatment that would not be effective without any sensitive patient potentially being excluded for a treatment that may have been effective. Further, any equivalent threshold or combination of thresholds that has been determined using a different training data set (such as e.g. a different cohort of patient-derived copy number features associated with known or assumed resistance status), and that has these properties may also be used.

REFERENCES

1. Macintyre G, Goranova T E, De Silva D, et al. Copy number signatures and mutational processes in ovarian carcinoma. Nat Genet. 2018; 50(9):1262-1270. doi: 10.1038/s41588-018-0179-8
2. Alexandrov L, Kim J, Haradhvala N J, Huang M N, Ng A W T, Boot A, et al. The Repertoire of Mutational Signatures in Human Cancer. bioRxiv 2018:322859 doi 10.1101/322859.
3. Schulze K, Imbeaud S, Letouzé E, Alexandrov L B, Calderaro J, Rebouissou S, et al. Exome sequencing of hepatocellular carcinomas identifies new mutational signatures and potential therapeutic targets. Nature Genetics 2015; 47:505 doi 10.1038/ng.3252.
4. Alexandrov L B, Nik-Zainal S, Wedge D C, Aparicio S A J R, Behjati S, Biankin A V, et al. Signatures of mutational processes in human cancer. Nature 2013; 500(7463):415-21 doi 10.1038/nature12477.
5. Mutch, D. G. et al. Randomized phase III trial of gemcitabine compared with pegylated liposomal doxorubicin in patients with platinum-resistant ovarian cancer. J. Clin. Oncol. 25, 2811-2818 (2007).
6. O'Byrne, K. J., Bliss, T. V. P. & Graham, J. D. A Phase III study of Doxil/Caylex versus paclitaxel in platinum treated taxane naive relapsed ovarian cancer. (2002).
7. Kaye, S. B. et al. Phase II, open-label, randomized, multicenter study comparing the efficacy and safety of olaparib, a poly (ADP-ribose) polymerase inhibitor, and pegylated liposomal doxorubicin in patients with BRCA1 or BRCA2 mutations and recurrent ovarian cancer. J. Clin. Oncol. 30, 372-379 (2012).
8. Ferrandina, G. et al. Phase III trial of gemcitabine compared with pegylated liposomal doxorubicin in progressive or recurrent ovarian cancer. J. Clin. Oncol. 26, 890-896 (2008).
9. Gordon, A. N., Tonda, M., Sun, S., Rackoff, W. & Doxil Study 30-49 Investigators. Long-term survival advantage for women treated with pegylated liposomal doxorubicin compared with topotecan in a phase 3 randomized study of recurrent and refractory epithelial ovarian cancer. Gynecol. Oncol. 95, 1-8 (2004).
10. Pujade-Lauraine, E. et al. AURELIA: A randomized phase III trial evaluating bevacizumab (BEV) plus chemotherapy (CT) for platinum (PT)-resistant recurrent ovarian cancer (OC). J. Clin. Orthod. 30, LBA5002-LBA5002 (2012).
11. Rose, P. et al. Phase 3 Study: Canfosfamide (C, TLK286) plus carboplatin (P) vs liposomal doxorubicin (D) as 2nd line therapy of platinum (P) resistant ovarian cancer (OC). J. Clin. Orthod. 25, LBA5529-LBA5529 (2007).
12. Bafaloukos, D. et al. A randomized phase II study of carboplatin plus pegylated liposomal doxorubicin versus carboplatin plus paclitaxel in platinum sensitive ovarian cancer patients: a Hellenic Cooperative Oncology Group study. 3MC Med. 8, 3 (2010).
13. Alberts, D. S. et al. Randomized trial of pegylated liposomal doxorubicin (PLD) plus carboplatin versus carboplatin in platinum-sensitive (PS) patients with recurrent epithelial ovarian or peritoneal carcinoma after failure of initial platinum-based chemotherapy (Southwest Oncology Group Protocol S0200). Gynecol. Oncol. 108, 90-94 (2008).
14. Ritz C, Baty F, Streibig J C, Gerhard D. Dose-Response Analysis Using R. *PLoS One* 2015; 10: e0146021.
15. Li H, Durbin R. Fast and accurate short read alignment with Burrows-Wheeler transform. *Bioinformatics* 2009; 25: 1754-1760.
16. Broad Institute. Picard toolkit. 2018.broadinstitute.github.io/picard/.
17. Scheinin I, Sie D, Bengtsson H, van de Wiel M A, Olshen A B, van Thuijl H F et al. DNA copy number analysis of fresh and formalin-fixed specimens by shallow whole-genome sequencing with identification and exclusion of problematic regions in the genome assembly. *Genome Res* 2014; 24: 2022-2032.
18. Grün B, Leisch F. FlexMix Version 2: Finite Mixtures with Concomitant Variables and Varying and Constant Parameters. *Journal of Statistical Software, Articles* 2008; 28: 1-35.
19. Gordon A N, Fleagle J T, Guthrie D, Parkin D E, Gore M E, Lacave A J. Recurrent epithelial ovarian carcinoma: a randomized phase III study of pegylated liposomal doxorubicin versus topotecan. *J Clin Oncol* 2001; 19: 3312-3322.
20. Rustin G J S, Vergote I, Eisenhauer E, Pujade-Lauraine E, Quinn M, Thigpen T et al. Definitions for response and progression in ovarian cancer clinical trials incorporating RECIST 1.1 and CA 125 agreed by the Gynecological Cancer Intergroup (GCIG). *Int J Gynecol Cancer* 2011; 21: 419-423.
21. Therneau T M. A Package for Survival Analysis in R. 2020 CRAN.R-project.org/package=survival.
22. Kassambara A, Kosinski M, Biecek P. survminer: Drawing Survival Curves using 'ggplot2'. 2019.CRAN.R-project.org/package=survminer.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A method for predicting the treatment response of treating a cancer in a patient, the method comprising:
   (a) obtaining a tumour copy number profile for the patient;
   (b) analysing the copy number profile to assess whether the characteristics of at least one copy number feature are indicative of the presence of focal amplifications in the tumour genome, wherein analysing the copy number profile comprises:
      i. quantifying, for each copy number event in the copy number profile, one or more copy number features selected from: the segment copy number, the copy number change-point, and the segment size,
      ii. obtaining one or more summarised measures for each quantified copy number feature, wherein the one or more summarised measures comprises the sum-of-posterior probabilities of the copy number feature value for each copy number event belonging to one or more predetermined distributions, and
      iii. for each copy number feature quantified, comparing the sum-of-posterior probabilities of the copy number feature value for each copy number event belonging to one or more predetermined distributions to a respective predetermined threshold;
   wherein the respective predetermined threshold is quantified by comparing the sum-of posterior probabilities for resistant and sensitive samples in a training cohort, and the one or more predetermined distributions comprise:
      one or more distributions (C1) of copy number change-point values centred around a value between 2 and 32,
      one or more distributions (C2) of copy number values centred around a value between 5 and 34, and/or
      one or more distributions (C3) of segment sizes centred around a value between 100,000 and 4,000,000 base pairs, and one or more distributions (C4) of segment sizes centred around a value between 12,000,000 and 80,000,000 bp;
   wherein the patient is predicted as being likely to be resistant to treatment with an agent that induces the formation of micronuclei if the characteristics of the at least one copy number features are indicative of the presence of focal amplifications in the tumour genome; and
   (c) upon determining that the characteristics of the at least one copy number features are not indicative of the presence of focal amplifications in the tumour genome, administering to the patient a genotoxic chemotherapeutic agent, DNA intercalating agent, a topoisomerase-II poison, or an anthracycline or doxorubicin.

2. The method of claim 1, wherein the patient is a patient diagnosed as having a carcinoma or a sarcoma, or wherein the patient is a patient diagnosed as having glioblastoma, lung cancer, oesophageal cancer, pancreatic cancer, breast cancer or ovarian cancer.

3. The method of claim 1, wherein the patient has high grade serous ovarian cancer (HGSOC) or triple negative breast cancer.

4. The method of claim 1, wherein the agent is liposomal doxorubicin.

5. The method of claim 1, wherein the tumour copy number profile for the patient has been obtained from a tumour sample from the patient or from a liquid biopsy sample from the patient.

6. The method of claim 1, wherein analysing the copy number profile to assess whether the characteristics of at least one copy number feature are indicative of the presence of focal amplifications in the tumour genome comprises:
   i. quantifying, for each copy number event in the copy number profile one or more further copy number features selected from: breakpoint count per x MB, where x is preferably 10, breakpoint count per chromosome arm, and length of segments with oscillating copy-number; and
   ii. obtaining one or more summarised measures for each further quantified copy number feature.

7. The method of claim 1, wherein the one or more summarised measures further comprises:
   i. for the copy number features selected from the segment copy number and the copy number change-point: a statistical measure of centrality of the distribution of values across copy number events, preferably the average or the median;

ii. the number or proportion of values across copy number events that are above and/or below a predetermined threshold;

iii. the maximum value across copy number events or the maximum value that is such that the proportion of copy number events that are at or above the value is above a predetermined threshold, and/or iv. for the segment size copy number feature: the minimum value across copy number events or the minimum value that is such that the proportion of copy number events that are at or below the value is above a predetermined threshold.

8. The method of claim 7, wherein analysing the copy number profile to assess whether the characteristics of at least one copy number feature are indicative of the presence of focal amplifications in the tumour genome comprises:

comparing an average, median or maximum segment copy number to a predetermined threshold, wherein the average, median or maximum segment copy number being above the predetermined threshold is indicative of the presence of focal amplifications in the tumour genome, preferably wherein the predetermined threshold is determined by comparing the average, median or maximum segment copy number between resistant and sensitive samples in a training cohort; and/or comparing the average, median or maximum copy number change-point to a predetermined threshold, wherein the average, median or maximum copy number change-point being above the predetermined threshold is indicative of the presence of focal amplifications in the tumour genome, preferably wherein the predetermined threshold is determined by comparing the average or median copy number change-point between resistant and sensitive samples in a training cohort.

9. The method of claim 7, wherein analysing the copy number profile to assess whether the characteristics of at least one copy number feature are indicative of the presence of focal amplifications in the tumour genome comprises:

comparing the number or proportion of events with a segment copy number above a first predetermined threshold to a second predetermined threshold, wherein the number or proportion of events being above the second predetermined threshold is indicative of the presence of focal amplifications in the tumour genome, preferably wherein the first and/or second predetermined thresholds are obtained by comparing the distribution of segment copy number for resistant and sensitive samples in a training cohort; and/or comparing the number or proportion of events with a copy number change-point above a first predetermined threshold to a second predetermined threshold, wherein the number or proportion of events being above the second predetermined threshold is indicative of the presence of focal amplifications in the tumour genome, preferably wherein the first and/or second predetermined thresholds are obtained by comparing the distribution of copy number change-point for resistant and sensitive samples in a training cohort; and/or comparing: (a) the proportion or number of events with a segment size above a first predetermined threshold to a second predetermined threshold, and also comparing: (b) the proportion or number of events with a segment size below a third predetermined threshold to a fourth predetermined threshold, wherein the proportions in (a) and (b) being above their respective predetermined thresholds is indicative of the presence of focal amplifications in the tumour genome, or comparing the sum of the proportion or number of events with a segment size above a first predetermined threshold and the proportion or number of events with a segment size below a third predetermined threshold to a fifth predetermined threshold, preferably wherein the first, second, third, fourth and/or fifth predetermined thresholds are obtained by comparing the distribution of segment size for resistant and sensitive samples in a training cohort.

10. The method of claim 1, wherein:

the one or more distributions (C1) of copy number change-point values centred around a value between 2 and 32, comprise one or more distributions centred around a value between 4 and 30, between 5 and 30, or between 6 and 30;

the one or more distributions (C2) of copy number values centred around a value between 5 and 34, comprise one or more distributions centred around a value between 6 and 34, between 7 and 34, between 6 and 32, between 7 and 32, or between 8 and 32; and/or the one or more distributions (C3) of segment sizes centred around a value between 100,000 and 4,000,000 base pairs, comprise one or more distributions centred around a value between 200,000 and 4,000,000 bp, between 300,000 and 4,000,000 bp, between 400,000 and 4,000,000 bp, between 100,000 and 3,000,000 bp, between 200,000 and 3,000,000 bp, between 300,000 and 3,000,000 bp, between 400,000 and 3,000,000 bp, between 100,000 and 2,500,000 bp, between 200,000 and 2,500,000 bp, between 300,000 and 2,500,000 bp or between 400,000 and 2,500,000 bp, and the one or more distributions (C4) of segment sizes centred around a value between 12,000,000 and 80,000,000 bp, comprise one or more distributions centred around a value between 15,000,000 and 60,000,000;

wherein the respective predetermined thresholds are quantified by comparing the sum-of-posterior probabilities for resistant and sensitive samples in a training cohort.

11. The method of claim 1, comprising obtaining a summarised measure that captures the contribution of multiple copy number features, and comparing the summarised measure to a predetermined threshold, wherein the summarised measure being above the predetermined threshold is indicative of the presence of focal amplifications.

12. A method of treating a cancer in a patient, the method comprising:

(a) obtaining a tumour copy number profile for the patient;

(b) analysing the copy number profile to assess whether the characteristics of at least one copy number feature are indicative of the presence of focal amplifications in the tumour genome;

wherein the at least one copy number feature is selected from: copy number change-point, segment size and segment copy number; and wherein the patient is predicted as being likely to be resistant to treatment with an agent that induces the formation of micronuclei if the characteristics of the at least one copy number features are indicative of the presence of focal amplifications in the tumour genome; and (c) upon determining that the characteristics of the at least one copy number features are not indicative of the presence of focal amplifications in the tumour genome, administering to the patient the agent that induces the formation of micronuclei, wherein the agent that induces the formation of micronuclei is a genotoxic chemotherapeutic agent, DNA intercalating agent, a topoisomerase-II poison, an anthracycline or doxorubicin;

wherein analysing the copy number profile to assess whether the characteristics of at least one copy number feature are indicative of the presence of focal amplifications in the tumour genome comprises obtaining a summarised measure that captures the contribution of multiple copy number features, and comparing the summarised measure to a predetermined threshold, wherein the summarised measure being above the predetermined threshold is indicative of the presence of focal amplifications, wherein the summarised measure is exposure ($E_i$) to a copy number signature i ($SbC_i$), where $E_i$ is the value that satisfies the equation:

$$PbC \approx E \times SbC \quad \text{(Equation 1)}$$

where:
- E is a vector of size n comprising coefficients E1 ..., n where Ei is the exposure to signature i;
- PbC is a vector of size c≥1, preferably 1≤c≤36, each element in the vector representing the sum-of-posterior probabilities of each copy number event in the copy number profile belonging to a component C, where each component C is a distribution of values for a copy number feature;
- SbC is a matrix of size c by n, each value representing the weight of a component C in a signature i.

13. The method of claim 12, wherein the components comprise:
(i) at least a component C1 that is a distribution of copy number change-point values centred around a value between 2 and 32;
(ii) at least one component C2 that is a distribution of copy number values centred around a value between 5 and 34;
(iii) at least one component C3 that is a distribution of segment sizes centred around a value between 100,000 and 4,000,000 base pairs and at least one component C4 that is a distribution of segment sizes centred around a value between 12,000,000 and 80,000,000 bp;
(iv) one or more components C1, one or more components C2, one or more components C3 and one or more components C4; or
(v) the components in the table below, or components that are distributions with mean (or λ) and/or standard deviations within 10%, within 5%, within 2% or within 1% of the distribution parameters the table below:

| Component No. | Distribution |
|---|---|
| cp1 | N(0.49452648, 0.15645341) |
| cp2 | N(0.96834666, 0.15629395) |
| cp3 | N(1.17859816, 0.22669911) |
| cp4 | N(1.82240751, 0.39907792) |
| cp5 | N(3.00685766, 1.03958107) |
| cp6 | N(7.3149416, 3.45921997) |
| cp7 | N(28.7346654, 22.0551593) |
| cn1 | N(0.99799839, 0.10280125) |
| cn2 | N(1.98135508, 0.12149214) |
| cn3 | N(2.56168152, 1.00230467) |
| cn4 | N(2.99108879, 0.1440896) |
| cn5 | N(3.97051928, 0.17145688) |
| cn6 | N(4.27164691, 1.58429331) |
| cn7 | N(8.39260927, 3.50149434) |
| cn8 | N(30.8672269, 23.15811) |
| ss1 | N(426861.918, 186924.872) |
| ss2 | N(1081858.4, 407302.128) |
| ss3 | N(2233029.82, 749092.036) |
| ss4 | N(4303321.09, 1115831.53) |
| ss5 | N(7304340.04, 1644306.83) |
| ss6 | N(10479327.2, 2972413.84) |
| ss7 | N(16419124.1, 5226151.49) |
| ss8 | N(29508322.4, 9703791.44) |
| ss9 | N(58638899, 20499001.4) |
| ss10 | N(118310989, 45210595) |
| bp1 | P(6.47E−05) |
| bp2 | P(1.25529082) |
| bp3 | P(4.07458306) |
| ct1 | P(0.06154321) |
| ct2 | P(2.62256735) |
| ct3 | P(7.77720192) |
| ct4 | P(17.5464903) |
| ct5 | P(33.5306827) |
| os1 | P(0.33948439) |
| os2 | P(2.62714528) |
| os3 | P(9.58714514). |

14. The method of claim 7, wherein the corresponding elements of SbC for each component are the corresponding weights defined in the table below, or weights within 10%, within 5%, within 2% or within 1% of the weights in the table, and wherein the components comprise the components in the table below and the corresponding elements of SbC are the corresponding weights defined in the table below

| Type | Component No | Distribution | Weight |
|---|---|---|---|
| Copy number change-point | cp1 | N(0.49452648, 0.15645341) | 2.220446e−16 |
| Copy number change-point | cp2 | N(0.96834666, 0.15629395) | 5.227448e+01 |
| Copy number change-point | cp3 | N(1.17859816, 0.22669911) | 1.844236e+01 |
| Copy number change-point | cp4 | N(1.82240751, 0.39907792) | 7.093089e−04 |
| Copy number change-point | cp5 | N(3.00685766, 1.03958107) | 2.256705e+02 |
| Copy number change-point | cp6 | N(7.3149416, 3.45921997) | 3.407536e+02 |
| Copy number change-point | cp7 | N(28.7346654, 22.0551593) | 1.094957e+02 |
| Copy number | cn1 | N(0.99799839, 0.10280125) | 1.796167e−12 |
| Copy number | cn2 | N(1.98135508, 0.12149214) | 6.025619e+01 |
| Copy number | cn3 | N(2.56168152, 1.00230467) | 4.030726e+01 |
| Copy number | cn4 | N(2.99108879, 0.1440896) | 1.377268e+02 |
| Copy number | cn5 | N(3.97051928, 0.17145688) | 5.498051e+01 |
| Copy number | cn6 | N(4.27164691, 1.58429331) | 1.601024e+02 |
| Copy number | cn7 | N(8.39260927, 3.50149434) | 2.473803e+02 |
| Copy number | cn8 | N(30.8672269, 23.15811) | 1.278820e+02 |
| Segment size | ss1 | N(426861.918, 186924.872) | 3.664985e+02 |

| Type | Component No | Distribution | Weight |
|---|---|---|---|
| Segment size | ss2 | N(1081858.4, 407302.128) | 2.200091e+02 |
| Segment size | ss3 | N(2233029.82, 749092.036) | 3.772309e+01 |
| Segment size | ss4 | N(4303321.09, 1115831.53) | 2.220446e−16 |
| Segment size | ss5 | N(7304340.04, 1644306.83) | 5.356412e+00 |
| Segment size | ss6 | N(10479327.2, 2972413.84) | 3.131356e−10 |
| Segment size | ss7 | N(16419124.1, 5226151.49) | 4.811576e+01 |
| Segment size | ss8 | N(29508322.4, 9703791.44) | 8.298639e+01 |
| Segment size | ss9 | N(58638899, 20499001.4) | 9.536135e+01 |
| Segment size | ss10 | N(118310989, 45210595) | 4.209353e−09 |
| Breakpoint count per 10 MB | bp1 | P(6.47E−05) | 7.331333e+02 |
| Breakpoint count per 10 MB | bp2 | P(1.25529082) | 2.952606e+02 |
| Breakpoint count per 10 MB | bp3 | P(4.07458306) | 5.698965e+01 |
| Breakpoint count per chromosome arm | ct1 | P(0.06154321) | 2.673626e+01 |
| Breakpoint count per chromosome arm | ct2 | P(2.62256735) | 5.015466e+01 |
| Breakpoint count per chromosome arm | ct3 | P(7.77720192) | 7.164583e+01 |
| Breakpoint count per chromosome arm | ct4 | P(17.5464903) | 7.987976e+00 |
| Breakpoint count per chromosome arm | ct5 | P(33.5306827) | 2.220446e−16 |
| Oscillating CN length | os1 | P(0.33948439) | 4.479586e+02 |
| Oscillating CN length | os2 | P(2.62714528) | 3.473049e+00 |
| Oscillating CN length | os3 | P(9.58714514) | 2.220446e−16. |

15. The method of claim 12, wherein the components comprise the components in the table below, or distributions with mean (or $\lambda$) and/or standard deviations within 10%, within 5%, within 2% or within 1% of the distribution parameters in the table below,

| Component No. | Distribution |
|---|---|
| cp1 | N(0.49452648, 0.15645341) |
| cp2 | N(0.96834666, 0.15629395) |
| cp3 | N(1.17859816, 0.22669911) |
| cp4 | N(1.82240751, 0.39907792) |
| cp5 | N(3.00685766, 1.03958107) |
| cp6 | N(7.3149416, 3.45921997) |
| cp7 | N(28.7346654, 22.0551593) |
| cn1 | N(0.99799839, 0.10280125) |
| cn2 | N(1.98135508, 0.12149214) |
| cn3 | N(2.56168152, 1.00230467) |
| cn4 | N(2.99108879, 0.1440896) |
| cn5 | N(3.97051928, 0.17145688) |
| cn6 | N(4.27164691, 1.58429331) |
| cn7 | N(8.39260927, 3.50149434) |
| cn8 | N(30.8672269, 23.15811) |
| ss1 | N(426861.918, 186924.872) |
| ss2 | N(1081858.4, 407302.128) |
| ss3 | N(2233029.82, 749092.036) |
| ss4 | N(4303321.09, 1115831.53) |
| ss5 | N(7304340.04, 1644306.83) |
| ss6 | N(10479327.2, 2972413.84) |
| ss7 | N(16419124.1, 5226151.49) |
| ss8 | N(29508322.4, 9703791.44) |
| ss9 | N(58638899, 20499001.4) |
| ss10 | N(118310989, 45210595) |
| bp1 | P(6.47E−05) |
| bp2 | P(1.25529082) |
| bp3 | P(4.07458306) |
| ct1 | P(0.06154321) |
| ct2 | P(2.62256735) |
| ct3 | P(7.77720192) |
| ct4 | P(17.5464903) |
| ct5 | P(33.5306827) |
| os1 | P(0.33948439) |
| os2 | P(2.62714528) |
| os3 | P(9.58714514) | and wherein the summarised measure is exposure to the copy number signature SbCi defined by said components and the corresponding weights below for signature 6, or weights within 10%, within 5%, within 2% or within 1% of the weights in the table below, and wherein SbC further comprises additional signatures defined by said components and corresponding weights for signatures 1-5, 7 in the table below, or weights within 10%, within 5%, within 2% or within 1% of the weights for signatures 1-5, 7 in the table below:

| Comp. No | Weight Sig. 6 | Weight Sig. 1 | Weight Sig. 2 | Weight Sig. 3 | Weight Sig. 4 | Weight Sig. 5 | Weight Sig. 7 |
|---|---|---|---|---|---|---|---|
| ss1 | 3.664985e+02 | 5.874998E−09 | 6.357651E+02 | 3.495885E+02 | 3.195265E+02 | 2.758839E+02 | 2.220446E−16 |
| ss2 | 2.200091e+02 | 3.919165E+01 | 9.344973E+02 | 2.107191E+02 | 5.132767E+02 | 4.911694E+02 | 1.175359E−09 |
| ss3 | 3.772309e+01 | 8.692671E+00 | 7.997478E+02 | 1.865006E+02 | 5.224959E+02 | 4.837410E+02 | 1.392389E+02 |
| ss4 | 2.220446e−16 | 1.186716E−12 | 4.102743E+02 | 1.792579E+02 | 2.559155E+02 | 2.224521E+02 | 2.443877E+02 |
| ss5 | 5.356412e+00 | 9.416554E−04 | 1.399407E+02 | 1.771104E+02 | 1.246349E+02 | 9.130593E+01 | 2.559156E+02 |
| ss6 | 3.131356e−10 | 1.134795E−02 | 1.056615E+02 | 2.384823E+02 | 1.104778E+02 | 3.804761E+01 | 3.082691E+02 |
| ss7 | 4.811576e+01 | 2.515102E+01 | 3.263778E+01 | 3.801034E+02 | 1.276619E+02 | 3.035091E+01 | 4.499549E+02 |
| ss8 | 8.298639e+01 | 2.815465E+02 | 2.220446E−16 | 3.145101E+02 | 7.575488E+01 | 1.659839E−14 | 4.609180E+02 |
| ss9 | 9.536135e+01 | 4.271319E+02 | 2.220446E−16 | 6.699405E+01 | 7.048058E−01 | 2.220446E−16 | 1.441790E+02 |
| ss10 | 4.209353e−09 | 2.163535E+02 | 1.208025E−01 | 6.462114E−10 | 2.220446E−16 | 1.884395E+00 | 2.220446E−16 |

| Comp. No | Weight Sig. 6 | Weight Sig. 1 | Weight Sig. 2 | Weight Sig. 3 | Weight Sig. 4 | Weight Sig. 5 | Weight Sig. 7 |
|---|---|---|---|---|---|---|---|
| bp1 | 7.331333e+02 | 5.922842E+03 | 4.201845E+01 | 8.765489E+02 | 1.458561E+02 | 6.562871E+01 | 1.451856E+03 |
| bp2 | 2.952606e+02 | 1.674698E+03 | 3.217679E+02 | 1.393995E+03 | 5.482652E+02 | 2.328218E+02 | 1.943561E+03 |
| bp3 | 5.698965e+01 | 5.342843E+00 | 3.403277E+02 | 8.479927E+01 | 1.959023E+02 | 1.740944E+02 | 1.737137E+00 |
| os1 | 4.479586e+02 | 2.220446E-16 | 6.504749E+02 | 6.404900E+02 | 1.503803E+03 | 1.552809E+03 | 5.291782E+02 |
| os2 | 3.473049e+00 | 2.220446E-16 | 2.183590E+02 | 9.403746E+01 | 9.638086E+01 | 4.639440E+01 | 6.390338E+01 |
| os3 | 2.220446e-16 | 2.220446E-16 | 2.485718E+01 | 3.924113E+00 | 4.551777E-02 | 2.220446E-16 | 2.304946E-09 |
| cp1 | 2.220446e-16 | 2.140049E-06 | 9.986209E-02 | 1.180214E+02 | 2.220446E-16 | 1.720462E+03 | 5.979281E-01 |
| cp2 | 5.227448e+01 | 8.456386E+01 | 1.750840E+03 | 1.106694E+03 | 2.220446E-16 | 3.713199E-02 | 1.065770E+03 |
| cp3 | 1.844236e+01 | 6.557840E+01 | 7.026403E+02 | 3.489020E+02 | 2.342685E+02 | 2.220446E-16 | 3.358230E+02 |
| cp4 | 7.093089e-04 | 9.879969E+01 | 3.949138E+02 | 3.544807E+02 | 1.286606E+03 | 2.220446E-16 | 1.497280E+02 |
| cp5 | 2.256705e+02 | 2.567242E+01 | 7.040137E+01 | 8.888528E+01 | 6.385500E+02 | 8.912176E+00 | 2.674814E-14 |
| cp6 | 3.407536e+02 | 6.187037E-01 | 4.608997E+00 | 3.738473E+00 | 3.835558E+01 | 2.578551E+00 | 2.220446E-16 |
| cp7 | 1.094957e+02 | 2.220446E-16 | 9.290701E-02 | 2.562223E-01 | 2.220446E-16 | 1.192290E-01 | 2.731235E-01 |
| cn1 | 1.796167e-12 | 2.220446E-16 | 2.220446E-16 | 6.538948E+02 | 2.220446E-16 | 9.459096E+01 | 2.220446E-16 |
| cn2 | 6.025619e+01 | 1.946635E+02 | 3.112491E+02 | 1.275464E+03 | 2.163790E+01 | 3.566195E+02 | 1.128208E+02 |
| cn3 | 4.030726e+01 | 2.403932E+02 | 6.226564E+02 | 4.149842E+02 | 2.750706E+02 | 6.783415E+01 | 4.923219E+02 |
| cn4 | 1.377268e+02 | 1.378518E+02 | 7.158619E+02 | 1.887778E+02 | 4.488714E-01 | 2.763153E+01 | 4.028007E+02 |
| cn5 | 5.498051e+01 | 4.254641E+01 | 2.016845E+02 | 2.220446E-16 | 1.923032E+02 | 2.220446E-16 | 1.784711E+02 |
| cn6 | 1.601024e+02 | 1.899706E+02 | 8.976670E+02 | 2.220446E-16 | 1.497681E+03 | 3.677175E+02 | 6.793631E+02 |
| cn7 | 2.473803e+02 | 1.195794E+01 | 3.100969E+01 | 2.220446E-16 | 3.025158E+02 | 1.618100E+01 | 9.051164E-13 |
| cn8 | 1.278820e+02 | 2.601461E-01 | 8.277609E-01 | 9.966975E-13 | 8.002977E-01 | 3.491317E-01 | 1.194772E+00 |
| ct1 | 2.673626e+01 | 5.143919E+02 | 3.071631E+01 | 1.713388E+00 | 2.220446E-16 | 1.311933E+01 | 2.878734E+01 |
| ct2 | 5.015466e+02 | 6.143409E+02 | 2.220446E-16 | 9.037079E+01 | 5.853353E+02 | 2.220446E-16 | 2.245124E+02 |
| ct3 | 7.164583e+01 | 1.868481E+01 | 6.673895E-05 | 1.878851E+02 | 6.898058E+01 | 8.387338E+00 | 2.583170E+02 |
| ct4 | 7.987976e+00 | 2.220446E-16 | 9.513077E+01 | 2.220446E-16 | 2.005521E+01 | 4.124064E+01 | 2.220446E-16 |
| ct5 | 2.220446e-16 | 2.220446E-16 | 3.569713E+01 | 2.220446E-16 | 3.141504E+00 | 3.494840E+00 | 2.220446E-16. |

16. The method of claim 15, wherein exposure to signature i is calculated using signatures 1, 2, 3, 4, 5, 6 and 7, or corresponding signatures, and the exposure Ei that is indicative of the presence of focal amplifications is that of signature 6.

17. The method of claim 12, wherein:
the patient is selected as a patient diagnosed as having a carcinoma or a sarcoma; or
the patient is selected as a patient diagnosed as having glioblastoma, lung cancer, oesophageal cancer, pancreatic cancer, breast cancer or ovarian cancer; or
the patient is selected as a patient having high grade serous ovarian cancer (HGSOC) or triple negative breast cancer.

18. The method of claim 12, wherein the agent is doxorubicin or liposomal doxorubicin.

19. The method of claim 12, wherein the tumour copy number profile for the patient has been obtained from a tumour sample from the patient or from a liquid biopsy sample from the patient.

20. A method of treating a cancer patient, the method comprising:
(a) obtaining a tumour copy number profile for the patient;
(b) analysing the copy number profile to assess whether the characteristics of at least one copy number feature are indicative of the presence of focal amplifications in the tumour genome;
wherein the at least one copy number feature is selected from: copy number change-point, segment size and segment copy number; and wherein the patient is predicted as being likely to be resistant to treatment with an agent that induces the formation of micronuclei if the characteristics of the at least one copy number features are indicative of the presence of focal amplifications in the tumour genome; and
(c) upon determining that the characteristics of the at least one copy number features are not indicative of the presence of focal amplifications in the tumour genome, administering to the patient the agent that induces the formation of micronuclei, wherein the agent that induces the formation of micronuclei is a genotoxic chemotherapeutic agent, DNA intercalating agent, a topoisomerase-II poison, an anthracycline or doxorubicin;
wherein analysing the copy number profile to assess whether the characteristics of at least one copy number feature are indicative of the presence of focal amplifications in the tumour genome comprises obtaining a summarised measure that captures the contribution of multiple copy number features, and comparing the summarised measure to a predetermined threshold, wherein the summarised measure being above the predetermined threshold is indicative of the presence of focal amplifications, wherein the summarised measure is exposure ($E_i$) to a copy number signature i ($SbC_i$), where $E_i$ is the value that satisfies the equation:

$$PbC \approx E \times SbC \quad \text{(Equation 1)}$$

where:
E is a vector of size n comprising coefficients E1 ..., n where Ei is the exposure to signature i;
PbC is a vector of size c≥1, preferably 1≤c≤36, each element in the vector representing the sum-of-posterior probabilities of each copy number event in the copy number profile belonging to a component C, where each component C is a distribution of values for a copy number feature;
SbC is a matrix of size c by n, each value representing the weight of a component C in a signature i; and
wherein the components comprise the components below with mean or λ within 10%, within 5%, within 2% or within 1% of the distribution parameters and standard deviations within 10%, within 5%, within 2% or within 1% of the distribution parameters, and wherein SbCi is the signature defined by the corresponding weights below or weights within 10%, within 5%, within 2% or within 1% of the weights below:

| Component No. | Distribution | Component No | Weight Sig. 6 |
|---|---|---|---|
| cp1 | N(0.49452648, 0.15645341) | ss1 | 3.664985e+02 |
| cp2 | N(0.96834666, 0.15629395) | ss2 | 2.200091e+02 |
| cp3 | N(1.17859816, 0.22669911) | ss3 | 3.772309e+01 |
| cp4 | N(1.82240751, 0.39907792) | ss4 | 2.220446e−16 |
| cp5 | N(3.00685766, 1.03958107) | ss5 | 5.356412e+00 |
| cp6 | N(7.3149416, 3.45921997) | ss6 | 3.131356e−10 |
| cp7 | N(28.7346654, 22.0551593) | ss7 | 4.811576e+01 |
| cn1 | N(0.99799839, 0.10280125) | ss8 | 8.298639e+01 |
| cn2 | N(1.98135508, 0.12149214) | ss9 | 9.536135e+01 |
| cn3 | N(2.56168152, 1.00230467) | ss10 | 4.209353e−09 |
| cn4 | N(2.99108879, 0.1440896) | bp1 | 7.331333e+02 |
| cn5 | N(3.97051928, 0.17145688) | bp2 | 2.952606e+02 |
| cn6 | N(4.27164691, 1.58429331) | bp3 | 5.698965e+01 |
| cn7 | N(8.39260927, 3.50149434) | os1 | 4.479586e+02 |
| cn8 | N(30.8672269, 23.15811) | os2 | 3.473049e+00 |
| ss1 | N(426861.918, 186924.872) | os3 | 2.220446e−16 |
| ss2 | N(1081858.4, 407302.128) | cp1 | 2.220446e−16 |
| ss3 | N(2233029.82, 749092.036) | cp2 | 5.227448e+01 |
| ss4 | N(4303321.09, 1115831.53) | cp3 | 1.844236e+01 |
| ss5 | N(7304340.04, 1644306.83) | cp4 | 7.093089e−04 |
| ss6 | N(10479327.2, 2972413.84) | cp5 | 2.256705e+02 |
| ss7 | N(16419124.1, 5226151.49) | cp6 | 3.407536e+02 |
| ss8 | N(29508322.4, 9703791.44) | cp7 | 1.094957e+02 |
| ss9 | N(58638899, 20499001.4) | cn1 | 1.796167e−12 |
| ss10 | N(118310989, 45210595) | cn2 | 6.025619e+01 |
| bp1 | P(6.47E−05) | cn3 | 4.030726e+01 |
| bp2 | P(1.25529082) | cn4 | 1.377268e+02 |
| bp3 | P(4.07458306) | cn5 | 5.498051e+01 |
| ct1 | P(0.06154321) | cn6 | 1.601024e+02 |
| ct2 | P(2.62256735) | cn7 | 2.473803e+02 |
| ct3 | P(7.77720192) | cn8 | 1.278820e+02 |
| ct4 | P(17.5464903) | ct1 | 2.673626e+01 |
| ct5 | P(33.5306827) | ct2 | 5.015466e+01 |
| os1 | P(0.33948439) | ct3 | 7.164583e+01 |
| os2 | P(2.62714528) | ct4 | 7.987976e+00 |
| os3 | P(9.58714514) | ct5 | 2.220446e−16. |

\* \* \* \* \*